(12) United States Patent
Han et al.

(10) Patent No.: US 12,234,259 B2
(45) Date of Patent: Feb. 25, 2025

(54) GLYCOCONJUGATION PROCESS

(71) Applicant: Pfizer Inc., New York, NY (US)

(72) Inventors: Mingming Han, Holly Springs, NC (US); Rajesh Kumar Kainthan, Tappan, NY (US); Jin-Hwan Kim, Suffern, NY (US); Avvari Krishna Prasad, Chapel Hill, NC (US)

(73) Assignee: PFIZER INC., New York, NY (US)

( * ) Notice: Subject to any disclaimer, the term of this patent is extended or adjusted under 35 U.S.C. 154(b) by 0 days.

(21) Appl. No.: 18/176,631

(22) Filed: Mar. 1, 2023

(65) Prior Publication Data
US 2023/0203091 A1    Jun. 29, 2023

Related U.S. Application Data

(63) Continuation of application No. 17/400,938, filed on Aug. 12, 2021, now Pat. No. 11,603,384, which is a continuation of application No. 16/923,154, filed on Jul. 8, 2020, now Pat. No. 11,117,928, which is a continuation of application No. 16/505,757, filed on Jul. 9, 2019, now Pat. No. 10,745,438, which is a continuation of application No. 14/652,723, filed as application No. PCT/IB2013/060933 on Dec. 13, 2013, now Pat. No. 10,392,420.

(60) Provisional application No. 61/740,311, filed on Dec. 20, 2012.

(51) Int. Cl.
| | | |
|---|---|---|
| C07K 1/107 | (2006.01) |
| A61K 39/09 | (2006.01) |
| A61K 39/095 | (2006.01) |
| A61K 47/64 | (2017.01) |
| C07H 3/06 | (2006.01) |
| C07K 14/22 | (2006.01) |
| C07K 14/315 | (2006.01) |
| C07K 14/34 | (2006.01) |
| A61K 39/00 | (2006.01) |

(52) U.S. Cl.
CPC ............ *C07K 1/1077* (2013.01); *A61K 39/09* (2013.01); *A61K 39/092* (2013.01); *A61K 39/095* (2013.01); *A61K 47/6415* (2017.08); *A61K 47/646* (2017.08); *C07H 3/06* (2013.01); *C07K 14/22* (2013.01); *C07K 14/315* (2013.01); *C07K 14/34* (2013.01); *A61K 2039/6037* (2013.01)

(58) Field of Classification Search
None
See application file for complete search history.

(56) References Cited

U.S. PATENT DOCUMENTS

| | | | |
|---|---|---|---|
| 9,107,872 B2 * | 8/2015 | Biemans | .................. A61P 37/00 |
| 2007/0065460 A1 * | 3/2007 | Hamidi | .................. A61K 47/61 |
| | | | 435/85 |

* cited by examiner

*Primary Examiner* — Dale R Miller

(57) ABSTRACT

The present disclosure relates generally to methods of preparing glycoconjugates containing a saccharide conjugated to a carrier protein by use of stable nitroxyl radical related agent/oxidant as an oxidizing agent, to immunogenic compositions comprising such glycoconjugates, and to methods for the use of such glycoconjugates and immunogenic compositions.

25 Claims, 7 Drawing Sheets

GLYCOCONJUGATION PROCESS

CROSS REFERENCE TO RELATED APPLICATIONS

This application is a Continuation application of U.S. Ser. No. 17/400,938, filed Aug. 12, 2021 (U.S. Pat. No. 11,603,384), which is a Continuation application of U.S. Ser. No. 16/923,154, filed Jul. 8, 2020 (U.S. Pat. No. 11,117,928), which is a Continuation application of U.S. Ser. No. 16/505,757, filed Jul. 9, 2019 (U.S. Pat. No. 10,745,438), which is a Continuation application of U.S. Ser. No. 14/652,723, filed Jun. 16, 2015 (U.S. Pat. No. 10,392,420), which is the National Stage of International Application No. PCT/IB2013/060933, filed Dec. 13, 2013, which claims the benefit of U.S. Provisional Application No. 61/740,311, filed Dec. 20, 2012, each of which is hereby incorporated by reference in its entirety.

FIELD

The present disclosure relates generally to methods of preparing glycoconjugates containing a saccharide conjugated to a carrier protein by use of TEMPO/NCS as an oxidizing agent, to immunogenic compositions comprising such glycoconjugates, and to methods for the use of such glycoconjugates and immunogenic compositions. The present disclosure also relates to methods of preparing glycoconjugates containing a saccharide conjugated to a carrier protein, by the use of stable nitroxyl or nitroxide radicals such as piperidine-N-oxy or pyrrolidine-N-oxy compounds in the presence of an oxidant to selectively oxidize primary hydroxyls of the said saccharide, to immunogenic compositions comprising such glycoconjugates, and to methods for the use of such glycoconjugates and immunogenic compositions.

BACKGROUND

Polysaccharide protein conjugate vaccines are made using polysaccharides, generally from the surface coat of bacteria, linked to protein carriers. The chemical bonding of the polysaccharide and protein carrier induces an immune response against bacteria displaying the polysaccharide contained within the vaccine on their surface, thus preventing disease. Accordingly, vaccination using polysaccharides from pathogenic bacteria is a potential strategy for boosting host immunity. The polysaccharides that cover bacteria vary greatly, even within a single species of bacteria. For example, in Streptococcus pneumoniae (a leading cause of meningitis, pneumonia, and severe invasive disease in infants and young children throughout the world) there are more than 90 different serotypes due to variation in the bacterial polysaccharide coat. Therefore, polysaccharide vaccines often consist of a panel of polysaccharides to increase protection.

Although polysaccharides are immunogenic on their own, conjugation of polysaccharides to protein carriers has been used to improve immunogenicity. The carrier protein can be either a related protein antigen from the target pathogen, boosting the specific immune response to that pathogen, or a generally immunogenic protein that serves more as an adjuvant or general immune response stimulant.

Multivalent pneumococcal polysaccharide-protein conjugate vaccines have been licensed for many years and have proved valuable in preventing pneumococcal disease in infants and have recently been recommended for adults.

SUMMARY

In one aspect, the present disclosure provides a method of making a glycoconjugate comprising a saccharide conjugated to a carrier protein, comprising the steps of: a) reacting a saccharide with 2,2,6,6-tetramethyl-1-piperidinyloxy (TEMPO) and N-chlorosuccinimide (NCS) in an aqueous solvent to produce an activated saccharide; and b) reacting the activated saccharide with a carrier protein comprising one or more amine groups. In a further aspect, the degree of oxidation of the activated saccharide ranges from 1 to 50, from 1 to 40, from 1 to 30, from 1 to 20, from 1 to 10, from 1 to 5, from 3 to 40, from 3 to 30, from 3 to 20, from 3 to 10, from 4 to 40, from 4 to 30, from 4 to 20, from 4 to 10, from 5 to 30, from 5 to 25, from 5 to 20, from 5 to 10, from 6 to 50, from 6 to 40, from 6 to 30, from 6 to 20, from 6 to 15, from 6 to 14, from 6 to 13, from 6 to 12, from 6 to 11, from 6 to 10, from 7 to 40, from 7 to 30, from 7 to 20, from 7 to 15, from 7 to 14, from 7 to 13, from 7 to 12, from 7 to 11, from 7 to 10, from 8 to 40, from 8 to 30, from 8 to 20, from 8 to 15, from 8 to 14, from 8 to 13, from 8 to 13, from 8 to 12, from 8 to 11, from 8 to 10, from 9 to 40, from 9 to 30, from 9 to 20, from 9 to 15, from 10 to 40, from 10 to 30, from 10 to 20, or from 10 to 15. In a further aspect, the degree of oxidation of the activated saccharide is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40.

In a further aspect, the present disclosure provides a method of making a glycoconjugate comprising a saccharide conjugated to a carrier protein, comprising the steps of: a) reacting a saccharide with a stable nitroxyl or nitroxide radical compound, such as piperidine-N-oxy or pyrrolidine-N-oxy compounds, in the presence of an oxidant to selectively oxidize primary hydroxyls of the said saccharide to produce an activated saccharide containing aldehyde groups; and b) reacting the activated saccharide with a carrier protein comprising one or more amine groups.

In said reaction, the actual oxidant is the N-oxoammonium salt, in a catalytic cycle. Preferably the stable nitroxyl or nitroxide radical compounds have the ability to selectively oxidize primary alcohol to aldehydes, in the presence of an oxidant, without over oxidation to carboxylic acids.

In an aspect, step a) of the reaction is carried out in aqueous solvent. In another aspect, step a) is carried out in aprotic solvent. In an aspect, step a) is carried out in DMSO (dimethylsulfoxide), Dimethylacetamide (DMA), Sulfolane, N-Methyl-2-pyrrolidone (NMP), Hexamethylphosphoramide (HMPA) or in DMF (dimethylformamide) solvent.

In an aspect, the unreacted aldehyde groups are converted back to primary alcohols during a capping step, using borohydride, after conjugation with the carrier protein, therefore minimizing the saccharide epitope modification during the modification steps involving oxidation followed by conjugation.

In an aspect, said stable nitroxyl or nitroxide radical compound are piperidine-N-oxy or pyrrolidine-N-oxy compounds. Preferably said compounds have the ability to selectively oxidize primary alcohols in the presence of an oxidant, to generate aldehyde groups, without affecting secondary hydroxyl groups. More preferably, said compounds have the ability to selectively oxidize primary alcohol in the presence of an oxidant, to generate aldehyde groups, without over oxidation to carboxyl groups.

In an aspect, said stable nitroxyl or nitroxide radical compound bears a TEMPO or a PROXYL (2,2,5,5-tetramethyl-1-pyrrolidinyloxy) moiety. Preferably said compound has the ability to selectively oxidize primary alcohol in the presence of an oxidant, to generate aldehyde groups, without affecting secondary hydroxyl groups. More preferably, said compound has the ability to selectively oxidize primary alcohols in the presence of an oxidant, to generate aldehyde groups, without over oxidation to carboxyl groups.

In an aspect, said stable nitroxyl radical compound is TEMPO or a derivative thereof. In an aspect, said stable nitroxyl radical compound is selected from the group consisting of TEMPO, 2,2,6,6-Tetramethyl-4-(methylsulfonyloxy)-1-piperidinooxy, 4-Phosphonooxy-TEMPO, 4-Oxo-TEMPO, 4-Methoxy-TEMPO, 4-Isothiocyanato-TEMPO, 4-(2-Iodoacetamido)-TEMPO free radical, 4-Hydroxy-TEMPO, 4-Cyano-TEMPO, 4-Carboxy-TEMPO, 4-(2-Bromoacetamido)-TEMPO, 4-Amino-TEMPO, 4-Acetamido-2,2,6,6-tetramethylpiperidine 1-oxyl. Preferably said stable nitroxyl radical compound is TEMPO.

In a further aspect, said stable nitroxyl radical compound is selected from the group consisting of 313-DOXYL-5α-cholestane, 5-DOXYL-stearic acid, 16-DOXYL-stearic acid, Methyl 5-DOXYL-stearate, 3-(Aminomethyl)-PROXYL, 3-Carbamoyl-PROXYL, 3-Carbamoyl-2,2,5,5-tetramethyl-3-pyrrolin-1-oxyl, 3-Carboxy-PROXYL, 3-Cyano-PROXYL.

In an aspect, said oxidant is a molecule bearing a N-halo moiety. Preferably said molecule has the ability to selectively oxidize primary alcohol in the presence of a nitroxyl radical compound.

In an aspect, said oxidant is selected from the group consisting of N-ChloroSuccinimide, N-Bromosuccinimide, N-Iodosuccinimide, Dichloroisocyanuric acid, 1,3,5-trichloro-1,3,5-triazinane-2,4,6-trione, Dibromoisocyanuric acid, 1,3,5-tribromo-1,3,5-triazinane-2,4,6-trione, Diiodoisocyanuric acid and 1,3,5-triiodo-1,3,5-triazinane-2,4,6-trione. Preferably said oxidant is N-Chlorosuccinimide.

In an aspect, the degree of oxidation of the activated saccharide ranges from 1 to 50, from 1 to 40, from 1 to 30, from 1 to 20, from 1 to 10, from 1 to 5, from 3 to 40, from 3 to 30, from 3 to 20, from 3 to 10, from 4 to 40, from 4 to 30, from 4 to 20, from 4 to 10, from 5 to 30, from 5 to 25, from 5 to 20, from 5 to 10, from 6 to 50, from 6 to 40, from 6 to 30, from 6 to 20, from 6 to 15, from 6 to 14, from 6 to 13, from 6 to 12, from 6 to 11, from 6 to 10, from 7 to 40, from 7 to 30, from 7 to 20, from 7 to 15, from 7 to 14, from 7 to 13, from 7 to 12, from 7 to 11, from 7 to 10, from 8 to 40, from 8 to 30, from 8 to 20, from 8 to 15, from 8 to 14, from 8 to 13, from 8 to 13, from 8 to 12, from 8 to 11, from 8 to 10, from 9 to 40, from 9 to 30, from 9 to 20, from 9 to 15, from 10 to 40, from 10 to 30, from 10 to 20, or from 10 to 15. In a further aspect, the degree of oxidation of the activated saccharide is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40.

In an aspect, the saccharide is reacted with 0.1 to 10 molar equivalents of oxidant. Preferably, the saccharide is reacted with 0.2 to 5, 0.5 to 2.5 or 0.5 to 1.5 molar equivalent of oxidant. In an aspect, the polysaccharide is reacted with about 0.2, 0.4, 0.6, 0.8, 1, 1.2, 1.4, 1.6, 1.8, 2, 2.2, 2.4, 2.6, 2.8, 3, 3.2, 3.4, 3.6, 3.8, 4, 4.2, 4.4, 4.6, 4.8 or 5 molar equivalents of oxidant.

In an aspect, the stable nitroxyl or nitroxide radical compound is present in a catalytic amount. In an aspect, the saccharide is reacted with less than about 0.3 molar equivalent of stable nitroxyl or nitroxide radical compound. In an aspect, the saccharide is reacted with less than about 0.005 molar equivalent of stable nitroxyl or nitroxide radical compound. In an aspect, the saccharide is reacted with about 0.005, 0.01, 0.05 or 0.1 molar equivalent of stable nitroxyl or nitroxide radical compound.

In a further aspect, the saccharide is a bacterial capsular polysaccharide. In another aspect the saccharide is a synthetically derived oligo or polysaccharide. In one aspect, the capsular polysaccharide is derived from *S. pneumonia* (Pn). In a further aspect, the capsular polysaccharide is selected from Pn-serotype 10A, Pn-serotype 12F, and Pn-serotype 33F capsular polysaccharides. For example, in one aspect the capsular polysaccharide is a Pn-serotype 12F capsular polysaccharide.

In a further aspect, the capsular polysaccharide is derived from *N. meningitidis*. In one aspect, the capsular polysaccharide is selected from meningococcal (Mn)-serotype A, C, W135, and Y capsular polysaccharides.

In a further aspect, the capsular polysaccharide is meningococcal (Mn)-serotype X capsular polysaccharide.

In a further aspect, the capsular polysaccharide is derived from Group B Streptococcus (GBS). In one aspect, the capsular polysaccharide is selected from GBS serotypes Ia, Ib, II, III, IV, V, VI, VII and VIII.

In one aspect, the present disclosure provides any of the methods disclosed herein wherein the carrier protein is a toxin from tetanus, diphtheria, pertussis, Pseudomonas, *E. coli*, *Staphylococcus* or *Streptococcus*. In one aspect the carrier protein is $CRM_{197}$.

In a further aspect, the present disclosure provides a method as described herein, wherein prior to step a), the saccharide is hydrolyzed to a molecular weight ranging from 100 to 400 kDa. For example, in one aspect, the molecular weight ranges from 100 to 350 kDa, from 100 to 300 kDa, from 100 to 250 kDa, from 100 to 200 kDa, from 100 to 150 kDa, from 200 to 400 kDa, from 200 to 350 kDa, from 200 to 300 kDa, from 200 to 250 kDa, from 300 to 400 kDa, or from 300 to 350 kDa.

In a further aspect, the present disclosure provides any of the methods provided herein further comprising the step of purifying the activated polysaccharide prior to step b). In a further aspect, the methods further comprise the step of adding a reducing agent following step b). In one aspect, the reducing agent is $NaCNBH_3$. In a further aspect, the methods further comprise the step of adding $NaBH_4$ following the addition of $NaCNBH_3$. In a further aspect, the method comprises a purification step following the addition of $NaBH_4$.

In another aspect, the present disclosure provides a glycoconjugate produced, or obtainable by any of the methods disclosed herein. For example, in one aspect the present disclosure provides a glycoconjugate comprising a saccharide conjugated to a carrier protein that is produced or obtainable by the method comprising the steps of: a) reacting a saccharide with 2,2,6,6-tetramethyl-1-piperidinyloxy (TEMPO) and N-chlorosuccinimide (NCS) in an aqueous solvent to produce an activated saccharide; and b) reacting the activated saccharide with a carrier protein comprising one or more amine groups. In a further aspect, the present disclosure provides a glycoconjugate comprising a saccharide conjugated to a carrier protein that is produced or obtainable by the method comprising the steps of: a) reacting a saccharide with a stable nitroxyl or nitroxide radical compound and an oxidant to produce an activated saccharide containing aldehyde groups; and b) reacting the activated saccharide with a carrier protein comprising one or more amine groups. Stable nitroxyl radical compounds and oxidant may be as defined at pages 2-4 above.

In a further aspect, the present disclosure provides an immunogenic composition comprising any of the glycoconjugates disclosed herein and a pharmaceutically acceptable excipient, carrier, or diluent. In a further aspect, the immunogenic composition comprises an additional antigen. In a further aspect, the additional antigen comprises a protein antigen or a glycoconjugate of a capsular polysaccharide derived from *S. pneumoniae*. For example, in one aspect the additional antigen comprises a glycoconjugate of a capsular polysaccharide selected from Pn-serotypes 1, 3, 4, 5, 6A, 6B, 7F, 8, 9V, 11A, 14, 15B, 18C, 19A, 19F, 22F, and 23F capsular polysaccharides. In a further aspect, the additional antigen comprises a protein antigen or a glycoconjugate of a capsular polysaccharide derived from *N. meningitidis*. In a further aspect, the additional antigen comprises a glycoconjugate of a capsular polysaccharide selected from serotypes A, C, W135 and Y capsular polysaccharides. In a further aspect, the additional antigen comprises a glycoconjugate of a capsular polysaccharide from serotype X capsular polysaccharides. In a further aspect, the additional antigen comprises a glycoconjugate of a capsular polysaccharide derived from Group B Streptococcus (GBS). In one aspect, the additional antigen comprises a glycoconjugate of a capsular polysaccharide selected from GBS serotypes Ia, Ib, II, III, IV, V, VI, VII and VIII.

In a further aspect, the present disclosure provides any of the immunogenic compositions disclosed herein, further comprising an adjuvant. In one aspect the adjuvant is an aluminum-based adjuvant. In a further aspect, the aluminum-based adjuvant is selected from the group consisting of aluminum phosphate, aluminum sulfate, and aluminum hydroxide.

In another aspect, the present disclosure provides a method of preventing, treating or ameliorating a bacterial infection, disease or condition in a subject, comprising administering to the subject an immunologically effective amount of any of the immunogenic compositions disclosed herein. In one aspect, the infection, disease or condition is associated with *S. pneumoniae* bacteria. In a further aspect, the infection, disease or condition is associated with *N. meningitidis* bacteria.

In another aspect, the present disclosure provides a method of inducing a protective immune response in a subject, comprising administering to the subject an immunologically effective amount of any of the immunogenic compositions disclosed herein.

In another aspect, the present disclosure provides an immunogenic composition comprising Pn-serotype 12F conjugated to a carrier protein wherein the conjugate is stable. For example, in one aspect, the present disclosure provides an immunogenic composition comprising Pn-serotype 12F conjugated to a carrier protein, wherein the amount of free Pn-serotype 12F polysaccharide in the composition is less than 35% after 120 days from when it was prepared. In a further aspect, the amount of free Pn-serotype 12F polysaccharide is less than 30%, less than 28%, less than 27%, less than 26%, or less than 25% after 120 days from when it was prepared. In a further aspect, the amount of free Pn-serotype 12F polysaccharide is less than 35%, less than 30%, less than 28%, less than 27%, less than 26%, or less than 25% after 90 days from when it was prepared. In a further aspect, the amount of free Pn-serotype 12F polysaccharide is less than 35%, less than 30%, less than 28%, less than 27%, less than 26%, or less than 25% after 60 days from when it was prepared. In a further aspect, the amount of free Pn-serotype 12F polysaccharide is less than 35%, less than 30%, less than 28%, less than 27%, less than 26%, or less than 25% after 30 days from when it was prepared. In a further aspect, the present disclosure provides a composition comprising Pn-serotype 3, 10A, or 33F conjugated to a carrier protein, wherein the amount of free Pn-serotype 3, 10A, or 33F polysaccharide, respectively, in the composition is less than 35% after 120 days from when it was prepared. In a further aspect, the amount of free Pn-serotype 3, 10A, or 33F polysaccharide is less than 30%, less than 28%, less than 27%, less than 26%, or less than 25% after 120 days from when it was prepared. In a further aspect, the amount of free Pn-serotype 3, 10A, or 33F polysaccharide is less than 35%, less than 30%, less than 28%, less than 27%, less than 26%, or less than 25% after 90 days from when it was prepared. In a further aspect, the amount of free Pn-serotype 3, 10A, or 33F polysaccharide is less than 35%, less than 30%, less than 28%, less than 27%, less than 26%, or less than 25% after 60 days from when it was prepared. In a further aspect, the amount of free Pn-serotype 3, 10A, or 33F polysaccharide is less than 35%, less than 30%, less than 28%, less than 27%, less than 26%, or less than 25% after 30 days from when it was prepared. In one aspect, the amount of free polysaccharide as discussed above is measured at 25° C. In one aspect, the carrier protein in the compositions disclosed above is a toxin from tetanus, diphtheria, pertussis, *Pseudomonas, E. coli, Staphylococcus* or *Streptococcus*. In a further aspect, the carrier protein is $CRM_{197}$.

The present disclosure further provides an immunogenic composition comprising any of such glycoconjugates disclosed above and a pharmaceutically acceptable excipient, carrier, or diluent. In a further aspect, such immunogenic compositions comprise an additional antigen. For example, in one aspect the additional antigen comprises a protein antigen or a glycoconjugate of a capsular polysaccharide derived from *S. pneumoniae*. In a further aspect, the additional antigen comprises a glycoconjugate of a capsular polysaccharide selected from Pn-serotypes 1, 3, 4, 5, 6A, 6B, 7F, 8, 9V, 11A, 14, 15B, 18C, 19A, 19F, 22F, and 23F capsular polysaccharides. In an even further aspect, the additional antigen comprises a protein antigen or a glycoconjugate of a capsular polysaccharide derived from *N. meningitidis*. In an even further aspect, the additional antigen comprises a glycoconjugate of a capsular polysaccharide selected from serotypes A, C, W135 and Y capsular polysaccharides. In a further aspect, the additional antigen comprises a glycoconjugate of a capsular polysaccharide from serotype X capsular polysaccharides. In a further aspect, the additional antigen comprises a glycoconjugate of a capsular polysaccharide from Group B Streptococcus (GBS). In one aspect, the capsular polysaccharide is selected from GBS serotypes Ia, Ib, II, III, IV, V, VI, VII and VIII.

In an even further aspect, such immunogenic compositions further comprise an adjuvant. For example, in one aspect the adjuvant is an aluminum-based adjuvant. In a further aspect, the aluminum-based adjuvant is selected from the group consisting of aluminum phosphate, aluminum sulfate, and aluminum hydroxide.

DETAILED DESCRIPTION

Figure 1:
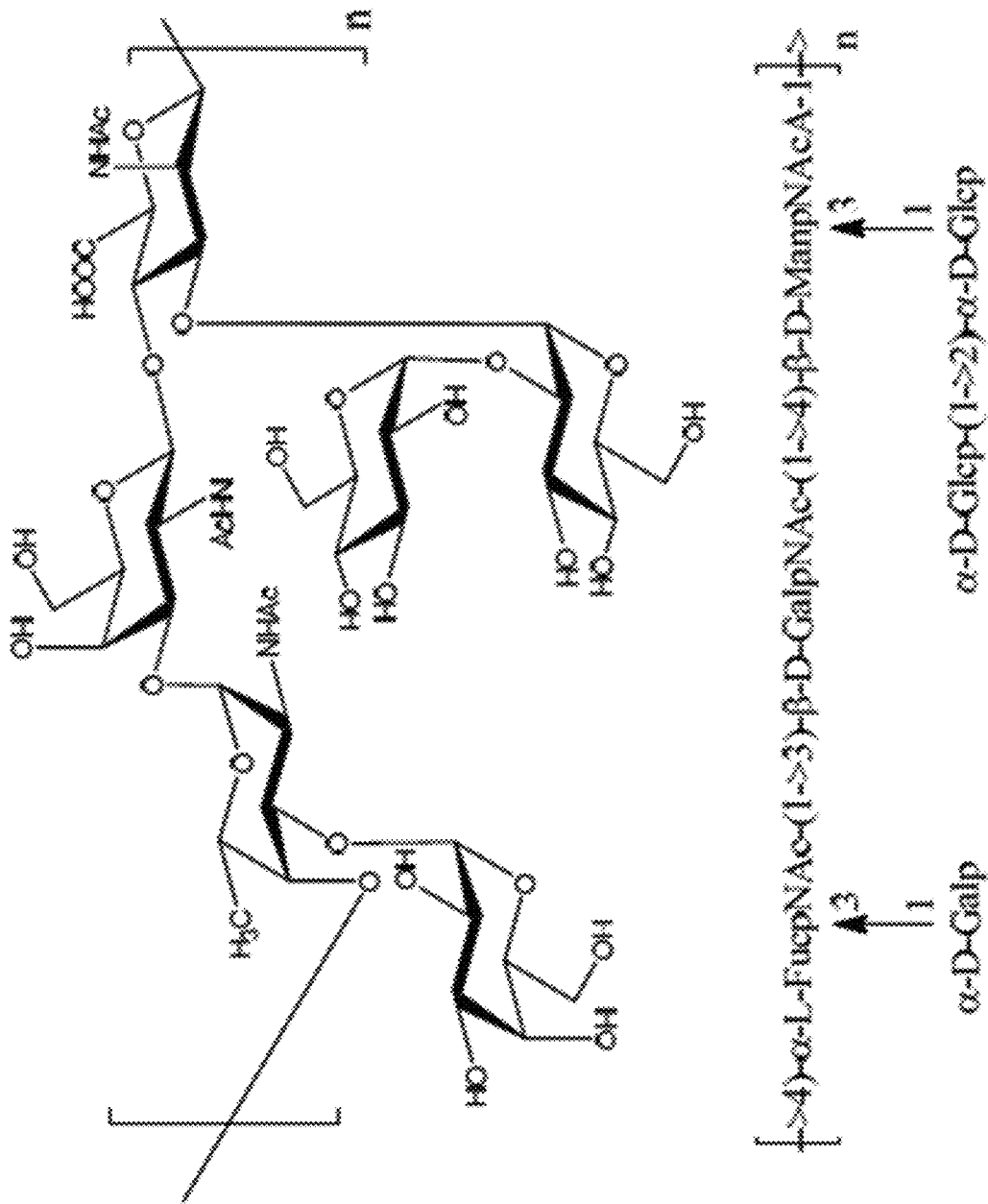
FIG. 1 shows the structure of the capsular polysaccharide of Pn-serotype 12F.

The present disclosure may be understood more readily by reference to the following detailed description of the various embodiments of the disclosure and the examples included herein. Unless defined otherwise, all technical and scientific terms used herein have the same meaning as commonly understood by one of ordinary skill in the art to which the disclosure pertains. Although any methods and materials similar or equivalent to those described herein can be used in the practice or testing of the present disclosure, certain preferred methods and materials are described herein. In describing the embodiments and in the claims, certain terminology will be used in accordance with the definitions set out below.

As used herein, the singular forms "a", "an", and "the" include plural references unless indicated otherwise. Thus, for example, references to "the method" includes one or more methods, and/or steps of the type described herein and/or which will become apparent to one of ordinary skill in the art upon reading this disclosure.

As used herein, the term "about" means within a statistically meaningful range of a value, such as a stated concentration range, time frame, molecular weight, temperature or pH. Such a range can be within an order of magnitude, typically within 20%, more typically within 10%, and even more typically within 5% or within 1% of a given value or range. Sometimes, such a range can be within the experimental error typical of standard methods used for the measurement and/or determination of a given value or range. The allowable variation encompassed by the term "about" will depend upon the particular system under study, and can be readily appreciated by one of ordinary skill in the art. Whenever a range is recited within this application, every whole number integer within the range is also contemplated as an embodiment of the disclosure.

It is noted that in this disclosure, terms such as "comprises," "comprised," "comprising," "contains," "containing" and the like can have the meaning attributed to them in U.S. patent law; e.g., they can mean "includes," "included," "including" and the like. Such terms refer to the inclusion of particular ingredients or set of ingredients without excluding any other ingredients. Terms such as "consisting essentially of" and "consists essentially of" have the meaning attributed to them in U.S. patent law, e.g., they allow for the inclusion of additional ingredients or steps that do not detract from the novel or basic characteristics of the disclosure, i.e., they exclude additional unrecited ingredients or steps that detract from the novel or basic characteristics of the disclosure. The terms "consists of" and "consisting of" have the meaning ascribed to them in U.S. patent law; namely, that these terms are closed ended. Accordingly, these terms refer to the inclusion of a particular ingredient or set of ingredients and the exclusion of all other ingredients.

As used herein, the term "saccharide" may be used to refer to a polysaccharide, an oligosaccharide, or a monosaccharide.

As used herein, the term "degree of oxidation" in reference to a saccharide refers to the ratio of the moles of saccharide repeat unit per mole of aldehyde. The degree of oxidation of a saccharide can be determined using routine methods known to those of skill in the art.

The term "conjugates" or "glycoconjugates" as used herein refers to a saccharide covalently conjugated to a carrier protein. Glycoconjugates of the disclosure and immunogenic compositions comprising them may contain some amount of free saccharide.

The term "free saccharide" as used herein means a saccharide that is not covalently conjugated to the carrier protein, but is nevertheless present in the glycoconjugate composition. The free saccharide may be non-covalently associated with (i.e., non-covalently bound to, adsorbed to, or entrapped in or with) the conjugated saccharide-carrier protein glycoconjugate. The terms "free polysaccharide" and "free capsular polysaccharide" may be used herein to convey the same meaning with respect to glycoconjugates wherein the saccharide is a polysaccharide or a capsular polysaccharide, respectively.

As used herein, "to conjugate," "conjugated" and "conjugating" refer to a process whereby a saccharide, for example a bacterial capsular polysaccharide, is covalently attached to a carrier molecule or carrier protein. The conjugation can be performed according to the methods described below or by other processes known in the art. Conjugation enhances the immunogenicity of the bacterial capsular polysaccharide.

The term "subject" refers to a mammal, including a human, or to a bird, fish, reptile, amphibian or any other animal. The term "subject" also includes household pets or research animals. Non-limiting examples of household pets and research animals include: dogs, cats, pigs, rabbits, rats, mice, gerbils, hamsters, guinea pigs, ferrets, monkeys, birds, snakes, lizards, fish, turtles, and frogs. The term "subject" also includes livestock animals. Non-limiting examples of livestock animals include: alpaca, bison, camel, cattle, deer, pigs, horses, llamas, mules, donkeys, sheep, goats, rabbits, reindeer, yak, chickens, geese, and turkeys.

Glycoconjugates

The present disclosure relates to methods of preparing glycoconjugates comprising a saccharide conjugated to a carrier protein, in particular by using a stable nitroxyl or nitroxide radial compound, to selectively oxidize primary alcohols of the saccharide to aldehydes, further using an oxidant. In an aspect, said stable nitroxyl radical compound are piperidine-N-oxy or pyrrolidine-N-oxy compounds. Preferably said compounds have the ability to selectively oxidize primary alcohol to aldehydes in the presence of an oxidant, without over oxidation to carboxylic acids and without affecting secondary hydroxyl groups. In an aspect, said stable nitroxyl radical compound is a molecule bearing a TEMPO or a PROXYL (2,2,5,5-tetramethyl-1-pyrrolidinyloxy) moiety. Preferably said molecule has the ability to selectively oxidize primary alcohol in the presence of an oxidant, to generate aldehyde groups, without affecting secondary hydroxyl groups. More preferably said molecule has the ability to selectively oxidize primary alcohol in the presence of an oxidant, to generate aldehyde groups, without over oxidation to carboxyl groups. In an aspect, said stable nitroxyl radical compound is selected from the groups consisting of TEMPO, 2,2,6,6-Tetramethyl-4-(methylsulfonyloxy)-1-piperidinooxy, 4-Phosphonooxy-TEMPO, 4-Oxo-TEMPO, 4-Methoxy-TEMPO, 4-Isothiocyanato-TEMPO, 4-(2-lodoacetamido)-TEMPO free radical, 4-Hydroxy-TEMPO, 4-Cyano-TEMPO, 4-Carboxy-TEMPO, 4-(2-Bromoacetamido)-TEMPO, 4-Amino-TEMPO, 4-Acetamido-2,2,6,6-tetramethylpiperidine 1-oxyl. Preferably said stable nitroxyl radical compound is TEMPO. In a further aspect, said stable nitroxyl radical compound is selected from the groups consisting of 3β-DOXYL-5α-cholestane, 5-DOXYL-stearic acid, 16-DOXYL-stearic acid, Methyl 5-DOXYL-stearate, 3-(Aminomethyl)-PROXYL, 3-Carbamoyl-PROXYL, 3-Carbamoyl-2,2,5,5-tetramethyl-3-pyrrolin-1-oxyl, 3-Carboxy-PROXYL, 3-Cyano-PROXYL. In an aspect, the oxidant is a molecule bearing a N-halo moiety. Preferably said molecule has the ability to selectively oxidize primary alcohol in the presence of a nitroxyl radical compound. In an aspect, said oxidant is selected from the group consisting of N-Chlorosuccinimide, N-Bromosuccinimide, N-lodosuccinimide, Dichloroisocyanuric acid, 1,3,5-trichloro-1,3,5-triazinane-2,4,6-trione, Dibromoisocyanuric acid, 1,3,5-tribromo-1,3,5-triazinane-2,4,6-trione, Diiodoisocyanuric acid and 1,3,5-triiodo-1,3, 5-triazinane-2,4,6-trione. Preferably said oxidant is N-Chlorosuccinimide.

In an aspect, the present disclosure relates to methods of preparing glycoconjugates comprising a saccharide conjugated to a carrier protein, in particular by using 2,2,6,6-Tetramethyl-1-piperidinyloxy free radical (TEMPO) to oxidize primary alcohols of the saccharide to aldehydes using N-Chlorosuccinimide (NCS) as the cooxidant.

In the glycoconjugates of the disclosure, the saccharide is selected from the group consisting of a polysaccharide, an oligosaccharide, and a monosaccharide, and the carrier protein is selected from any suitable carrier as further described herein or known to those of skill in the art. In some embodiments, the saccharide is a polysaccharide, in particular a bacterial capsular polysaccharide, such as *Streptococcus pneumoniae* serotype 10A (Pn-serotype 10A), Pn-serotype 12F, or Pn-serotype 33F. In some such embodiments, the carrier protein is $CRM_{197}$.

Capsular polysaccharides can be prepared by standard techniques known to those skilled in the art. For example, capsular polysaccharides can be prepared from a variety of serotypes, such as 1, 3, 4, 5, 6A, 6B, 7F, 8, 9V, 10A, 11A, 12F, 14, 15B, 18C, 19A, 19F, 22F, 23F and 33F of *Streptococcus pneumoniae*. These pneumococcal conjugates are prepared by separate processes and formulated into a single dosage formulation. For example, in one embodiment, each pneumococcal polysaccharide serotype is grown in a soy-based medium. The individual polysaccharides are then purified through centrifugation, precipitation, ultra-filtration, and column chromatography. The purified polysaccharides are chemically activated to make the saccharides (i.e. activated saccharides) capable of reacting with the carrier protein. Once activated, each capsular polysaccharide is separately conjugated to a carrier protein to form a glycoconjugate. In one embodiment, each capsular polysaccharide is conjugated to the same carrier protein. The chemical activation of the polysaccharides and subsequent conjugation to the carrier protein can be achieved by conventional means. See, for example, U.S. Pat. Nos. 4,673,574, 4,902, 506, 7,709,001, and 7,955,605.

In one embodiment, the glycoconjugate of the disclosure has a molecular weight of between about 50 kDa and about 20,000 kDa. In another embodiment, the glycoconjugate has a molecular weight of between about 200 kDa and about 10,000 kDa. In another embodiment, the glycoconjugate has a molecular weight of between about 500 kDa and about 5,000 kDa. In one embodiment, the glycoconjugate has a molecular weight of between about 1,000 kDa and about 3,000 kDa. In other embodiments the glycoconjugate has a molecular weight of between about 600 kDa and about 2800 kDa; between about 700 kDa and about 2700 kDa; between about 1000 kDa and about 2000 kDa; between about 1800 kDa and about 2500 kDa; between about 1100 kDa and about 2200 kDa; between about 1900 kDa and about 2700 kDa; between about 1200 kDa and about 2400 kDa; between about 1700 kDa and about 2600 kDa; between about 1300 kDa and about 2600 kDa; between about 1600 kDa and about 3000 kDa. Any whole number integer within any of the above ranges is contemplated as an embodiment of the disclosure.

Novel features of the glycoconjugates of the disclosure include the molecular weight profiles of the saccharides and resulting conjugates, the ratio of conjugated lysines per carrier protein and number of lysines covalently linked to the polysaccharide, the number of covalent linkages between the carrier protein and the saccharide as a function of repeat units of the saccharide, and the relative amount of free saccharide compared to the total saccharide.

In another embodiment, the polysaccharide is a capsular polysaccharide derived from *Neisseria meningitidis*. In some such embodiments, the capsular polysaccharide is selected from the group consisting of serotype A, B, C, W135, X and Y capsular polysaccharides of *N. meningitidis*. In one such embodiment, the capsular polysaccharide is a serotype C capsular polysaccharide. In another such embodiment, the capsular polysaccharide is a serotype W135 capsular polysaccharide. In another such embodiment, the capsular polysaccharide is a serotype Y capsular polysaccharide.

In some embodiments, the glycoconjugate of the disclosure comprises a bacterial capsular polysaccharide, wherein the capsular polysaccharide has a molecular weight of between 10 kDa and 2,000 kDa or between 50 kDa and 1,000 kDa. In some such embodiments, the capsular polysaccharide is derived from *S. pneumoniae* or *N. meningitidis*. In some such embodiments, the capsular polysaccharide is derived from *S. pneumoniae* and is selected from the group consisting of serotype 1, 3, 4, 5, 6A, 6B, 7F, 8, 9V, 10A, 11A, 12F, 14, 15B, 18C, 19A, 19F, 22F, 23F and 33F capsular polysaccharides. In other such embodiments, the capsular polysaccharide is derived from *N. meningitidis* and is selected from the group consisting of serotype A, B, C, W135, X and Y capsular polysaccharides.

In one embodiment, the disclosure provides a glycoconjugate comprising a capsular polysaccharide covalently conjugated to a carrier protein, having one or more of the following features: the polysaccharide has a molecular weight of between 50 kDa and 1,000 kDa; the glycoconjugate has a molecular weight of between 1,000 kDa to 3,000 KDa; and the conjugate comprises less than about 45% free polysaccharide relative to total polysaccharide. In some embodiments, the polysaccharide has a molecular weight of between 10 kDa and 2,000 kDa. In some embodiments the glycoconjugate has a molecular weight of between 50 kDa and 20,000 kDa. In other embodiments the glycoconjugate has a molecular weight of between 200 kDa and 10,000 kDa. In other embodiments, the conjugate comprises less than about 30%, 20%, 15%, 10%, or 5% free polysaccharide relative to total polysaccharide. The amount of free polysaccharide can be measured as a function of time, for example after 10, 20, 30, 40, 50, 60, 70, 80, 90, or 120 days, or even longer, after the conjugate was prepared.

The number of lysine residues in the carrier protein conjugated to the saccharide can be characterized as a range of conjugated lysines, which may be expressed as a molar ratio. For example, in an immunogenic composition where 4 to 15 lysine residues of $CRM_{197}$ are covalently linked to the saccharide, the molar ratio of conjugated lysines to $CRM_{197}$ in the glycoconjugate is between about 10:1 to about 40:1. In an immunogenic composition where 2 to 20 lysine residues of $CRM_{197}$ are covalently linked to the saccharide, the molar ratio of conjugated lysines to $CRM_{197}$ in the glycoconjugate is between about 5:1 to about 50:1.

In one embodiment, the molar ratio of conjugated lysines to carrier protein is from about 10:1 to about 25:1. In some such embodiments, the carrier protein is $CRM_{197}$. In one embodiment, the saccharide:carrier protein ratio (w/w) is between 0.2 and 4. In another embodiment, the saccharide:carrier protein ratio (w/w) is between 1.1 and 1.7. In some embodiments, the saccharide is a bacterial capsular polysaccharide, and the saccharide:carrier protein ratio (w/w) is between 0.2 and 4. In other embodiments, the saccharide is a bacterial capsular polysaccharide, and the saccharide:carrier protein ratio (w/w) is between 1.1 and 1.7. In some such embodiments, the carrier protein is $CRM_{197}$.

The frequency of attachment of the saccharide chain to a lysine on the carrier protein is another parameter for characterizing the glycoconjugates of the disclosure. For example, in one embodiment, there is at least one covalent linkage between the carrier protein and the polysaccharide for every 100 saccharide repeat units of the polysaccharide. In one embodiment, there is at least one covalent linkage between the carrier protein and the polysaccharide for every 50 saccharide repeat units of the polysaccharide. In one embodiment, there is at least one covalent linkage between the carrier protein and the polysaccharide for every 25 saccharide repeat units of the polysaccharide. In another embodiment, the covalent linkage between the carrier protein and the polysaccharide occurs at least once in every 4 saccharide repeat units of the polysaccharide. In another embodiment, the covalent linkage between the carrier protein and the polysaccharide occurs at least once in every 10 saccharide repeat units of the polysaccharide. In a further embodiment, the covalent linkage between the carrier protein and the polysaccharide occurs at least once in every 15 saccharide repeat units of the polysaccharide.

In frequent embodiments, the carrier protein is $CRM_{197}$ and the covalent linkage between the $CRM_{197}$ and the polysaccharide occurs at least once in every 4, 10, 15 or 25 saccharide repeat units of the polysaccharide. In some such embodiments, the polysaccharide is a bacterial capsular polysaccharide, for example a capsular polysaccharide derived from *S. pneumoniae* or *N. meningitidis* bacteria.

In other embodiments, the conjugate comprises at least one covalent linkage between the carrier protein and saccharide for every 5 to 10 saccharide repeat units; every 2 to 7 saccharide repeat units; every 3 to 8 saccharide repeat units; every 4 to 9 saccharide repeat units; every 6 to 11 saccharide repeat units; every 7 to 12 saccharide repeat units; every 8 to 13 saccharide repeat units; every 9 to 14 saccharide repeat units; every 10 to 15 saccharide repeat units; every 2 to 6 saccharide repeat units, every 3 to 7 saccharide repeat units; every 4 to 8 saccharide repeat units; every 6 to 10 saccharide repeat units; every 7 to 11 saccharide repeat units; every 8 to 12 saccharide repeat units; every 9 to 13 saccharide repeat units; every 10 to 14 saccharide repeat units; every 10 to 20 saccharide repeat units; or every 4 to 25 saccharide repeat units.

In another embodiment, at least one linkage between carrier protein and saccharide occurs for every 2, 3, 4, 5, 6, 7, 8, 9, 10, 11, 12, 13, 14, 15, 16, 17, 18, 19, 20, 21, 22, 23, 24 or 25 saccharide repeat units of the polysaccharide.

In one embodiment, the glycoconjugate of the disclosure comprises at least one covalent linkage between the carrier protein and the polysaccharide for every 25 saccharide repeat units of the polysaccharide. In another embodiment, the covalent linkage between the carrier protein and the polysaccharide occurs at least once in every 4 saccharide repeat units of the polysaccharide. In another embodiment, the covalent linkage between the carrier protein and the polysaccharide occurs at least once in every 10 saccharide repeat units of the polysaccharide. In a further embodiment, the covalent linkage between the carrier protein and the polysaccharide occurs at least once in every 15 saccharide repeat units of the polysaccharide.

In one embodiment, the glycoconjugate comprises less than about 45% free saccharide compared to the total amount of saccharide. In another embodiment, the glycoconjugate comprises less than about 30% free saccharide compared to the total amount of saccharide. In another embodiment, the glycoconjugate comprises less than about 20% free saccharide compared to the total amount of saccharide. In a further embodiment, the glycoconjugate comprises less than about 10% free saccharide compared to the total amount of saccharide. In another embodiment, the glycoconjugate comprises less than about 5% free saccharide compared to the total amount of saccharide.

In another embodiment, the glycoconjugate comprises less than about 20 mole % of carrier protein residues compared to the total amount of glycoconjugate.

In another aspect, the disclosure provides an immunogenic composition comprising a glycoconjugate of the disclosure and at least one of an adjuvant, diluent or carrier.

In one embodiment, the disclosure provides an immunogenic composition comprising a glycoconjugate of the disclosure and at least one of an adjuvant, diluent or carrier, wherein the glycoconjugate comprises a bacterial capsular polysaccharide covalently conjugated to a carrier protein. In some such embodiments, the capsular polysaccharide is derived from *S. pneumoniae* or *N. meningitidis*.

In some embodiments, the immunogenic composition comprises an adjuvant. In some such embodiments, the adjuvant is an aluminum-based adjuvant selected from the group consisting of aluminum phosphate, aluminum sulfate and aluminum hydroxide. In one embodiment, the immunogenic composition comprises the adjuvant aluminum phosphate.

In some embodiments, the glycoconjugates or immunogenic compositions of the disclosure can be used to generate antibodies that are functional as measured by killing bacteria in an animal efficacy model or via an opsonophagocytic killing assay.

In one embodiment, the disclosure provides a method of inducing an immune response in a subject, comprising administering to the subject an immunologically effective amount of an immunogenic composition of the disclosure as described herein. In another aspect, the disclosure provides a method for inducing an immune response against a pathogenic bacterium in a subject, comprising administering to the subject an immunologically effective amount of an immunogenic composition as described herein. In another aspect, the disclosure provides a method for preventing or ameliorating a disease or condition caused by a pathogenic bacterium in a subject, comprising administering to the subject an immunologically effective amount of an immunogenic composition as described herein. In another aspect, the disclosure provides a method for reducing the severity of at least one symptom of a disease or condition caused by infection with a pathogenic bacterium in a subject, comprising administering to the subject an immunologically effective amount of an immunogenic composition as described herein. In some embodiments, the pathogenic bacterium is *S. pneumoniae* or *N. meningitidis*.

In addition, the present disclosure provides methods for inducing an immune response against *S. pneumoniae* or *N. meningitidis* bacteria, methods for preventing a disease caused by *S. pneumoniae* or *N. meningitidis* bacteria, and methods for reducing the severity of at least one symptom of a disease caused by infection with *S. pneumoniae* or *N. meningitidis* bacteria.

Saccharides

Saccharides include polysaccharides, oligosaccharides and monosaccharides. In some embodiments, the saccharide is a polysaccharide, in particular a bacterial capsular polysaccharide.

The molecular weight of the capsular polysaccharide is a consideration for use in immunogenic compositions. High molecular weight capsular polysaccharides are able to induce certain antibody immune responses due to a higher valence of the epitopes present on the antigenic surface. The isolation and purification of high molecular weight capsular polysaccharides is contemplated for use in the conjugates, compositions and methods of the present disclosure.

In one embodiment, the capsular polysaccharide has a molecular weight of between 10 kDa and 2,000 kDa. In one embodiment, the capsular polysaccharide has a molecular weight of between 50 kDa and 1,000 kDa. In another embodiment, the capsular polysaccharide has a molecular weight of between 50 kDa to 300 kDa. In another embodiment, the capsular polysaccharide has a molecular weight of between 70 kDa to 300 kDa. In further embodiments, the capsular polysaccharide has a molecular weight of between 90 kDa to 250 kDa; 90 kDa to 150 kDa; 90 kDa to 120 kDa; 80 kDa to 120 kDa; 70 kDa to 100 kDa; 70 kDa to 110 kDa; 70 kDa to 120 kDa; 70 kDa to 130 kDa; 70 kDa to 140 kDa; 70 kDa to 150 kDa; 70 kDa to 160 kDa; 80 kDa to 110 kDa; 80 kDa to 120 kDa; 80 kDa to 130 kDa; 80 kDa to 140 kDa; 80 kDa to 150 kDa; 80 kDa to 160 kDa; 90 kDa to 110 kDa; 90 kDa to 120 kDa; 90 kDa to 130 kDa; 90 kDa to 140 kDa; 90 kDa to 150 kDa; 90 kDa to 160 kDa; 100 kDa to 120 kDa; 100 kDa to 130 kDa; 100 kDa to 140 kDa; 100 kDa to 150 kDa; 100 kDa to 160 kDa; and similar desired molecular weight ranges. Any whole number integer within any of the above ranges is contemplated as an embodiment of the disclosure.

Figure 3:
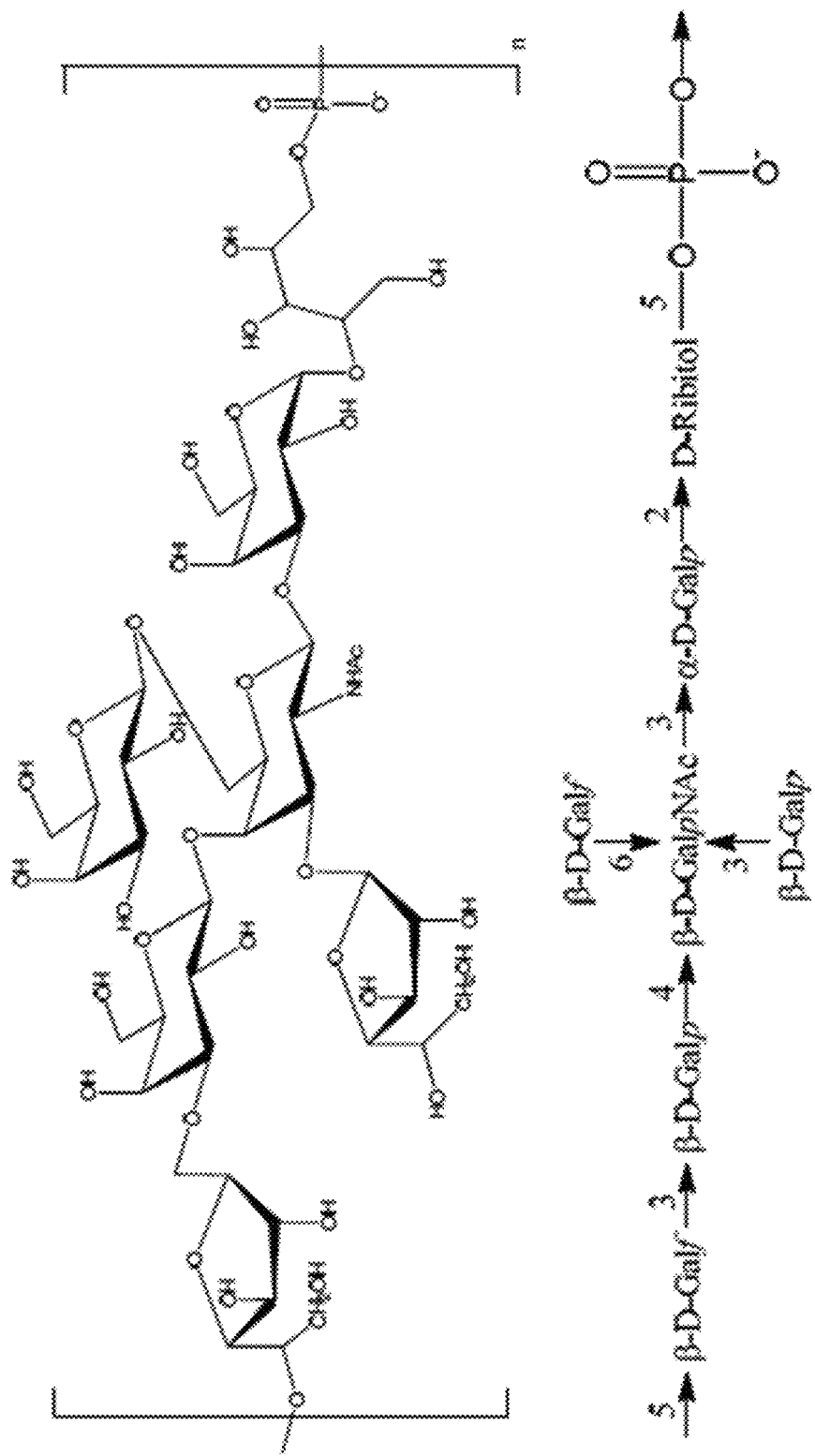
FIG. 3 shows the structure of the capsular polysaccharide of Pn-serotype 10A.
Figure 4:
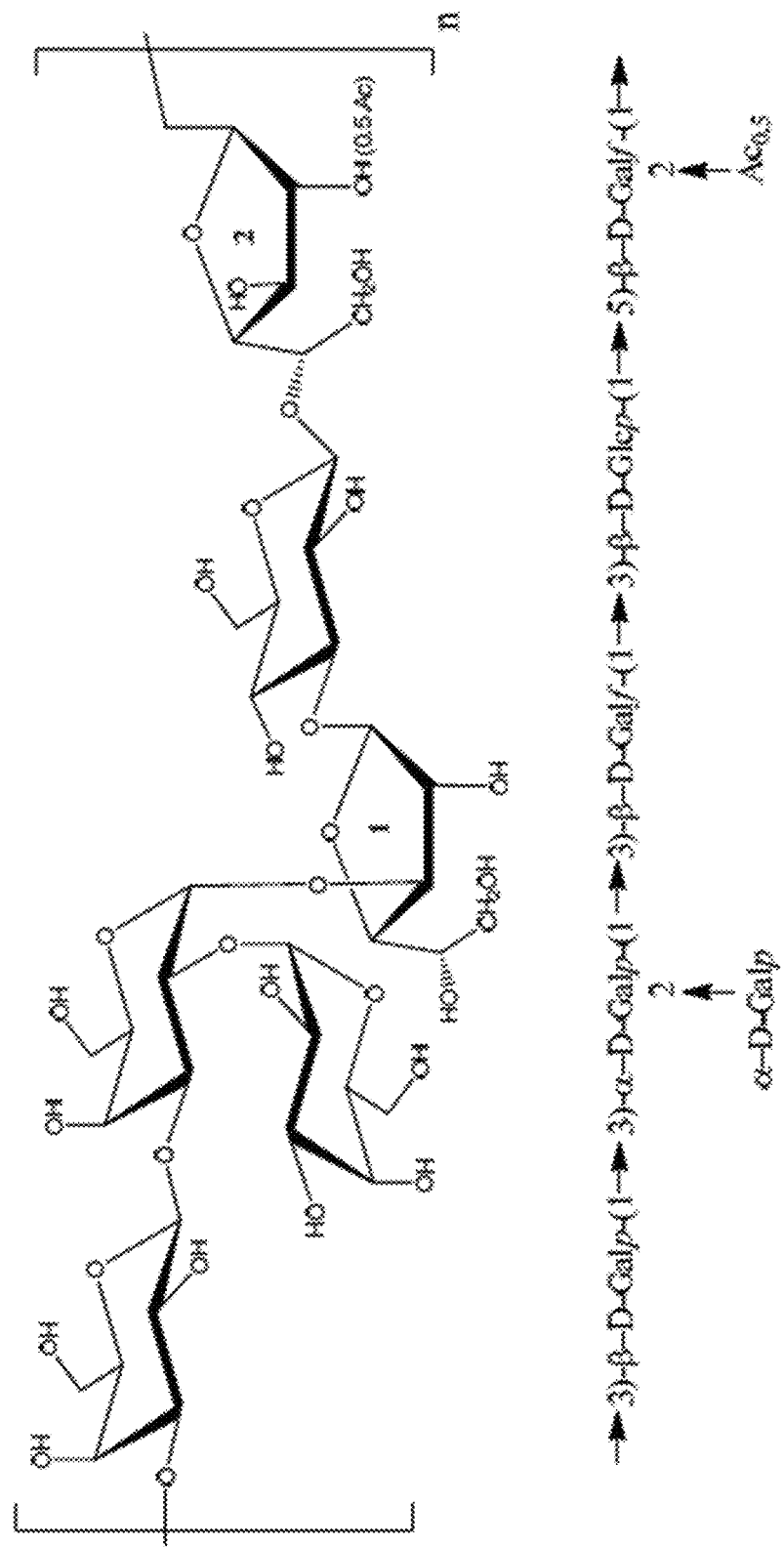
FIG. 4 shows the structure of the capsular polysaccharide of Pn-serotype 33F.
Figure 5:
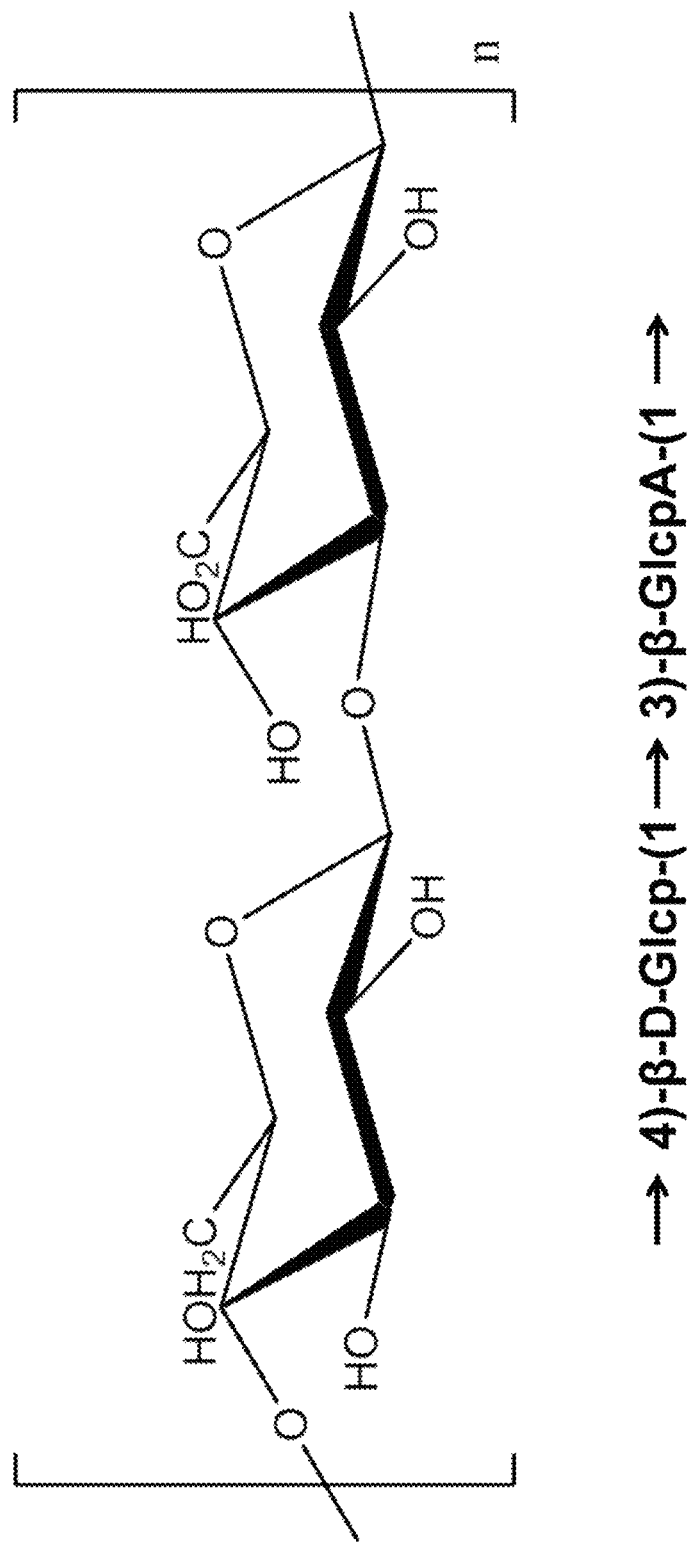
FIG. 5 shows the structure of the capsular polysaccharide of Pn-serotype 3.

The capsular polysaccharide of *S. pneumoniae*, Serotype 12F (Pn-serotype 12F) has the structure shown in FIG. 1. The capsular polysaccharide of *S. pneumoniae*, Serotype 10A (Pn-serotype 10A) has the structure shown in FIG. 3. The capsular polysaccharide of *S. pneumoniae*, Serotype 33F (Pn-serotype 33F) has the structure shown in FIG. 4. The capsular polysaccharide of *S. pneumoniae*, Serotype 3 (Pn-serotype 3) has the structure shown in FIG. 5.

In some embodiments, the capsular polysaccharides, glycoconjugates or immunogenic compositions of the disclosure are used to generate antibodies that are functional as measured by the killing of bacteria in an animal efficacy model or an opsonophagocytic killing assay that demonstrates that the antibodies kill the bacteria. Capsular polysaccharides can be obtained directly from bacteria using isolation procedures known to one of ordinary skill in the art. See, e.g., Fournier et al. (1984), supra; Fournier et al. (1987) *Ann. Inst. Pasteur/Microbiol.* 138:561-567; U.S. Patent Application Publication No, 2007/0141077; and Int'l Patent Application Publication No. WO 00/56357; each of which is incorporated herein by reference as if set forth in its entirety). In addition, they can be produced using synthetic protocols. Moreover, capsular polysaccharide can be recombinantly produced using genetic engineering procedures also known to one of ordinary skill in the art (see, Sau et al. (1997) *Microbiology* 143:2395-2405; and U.S. Pat. No. 6,027,925; each of which is incorporated herein by reference as if set forth in its entirety). *S. pneumoniae* or *N. meningitides* strains can be used to make the respective polysaccharides that are obtained either from established culture collections or clinical specimens.

Carrier Proteins

Another component of the glycoconjugate of the disclosure is a carrier protein to which the saccharide is conjugated. The term "protein carrier" or "carrier protein" or "carrier" refers to any protein molecule that may be conjugated to an antigen (such as a capsular polysaccharide) against which an immune response is desired.

Conjugation to a carrier can enhance the immunogenicity of the antigen. Protein carriers for the antigens can be toxins, toxoids or any mutant cross-reactive material (CRM) of the toxin from tetanus, diphtheria, pertussis, *Pseudomonas, E. coli, Staphylococcus* and *Streptococcus*. In one embodiment, a carrier is of diphtheria toxoid $CRM_{197}$, derived from *C. diphtheriae* strain C7 (8197), which produces $CRM_{197}$ protein. This strain has ATCC accession No. 53281. A method for producing $CRM_{197}$ is described in U.S. Pat. No. 5,614,382, which is incorporated herein by reference as if set forth in its entirety. Alternatively, a fragment or epitope of the protein carrier or other immunogenic protein can be used. For example, a haptenic antigen can be coupled to a T-cell epitope of a bacterial toxin, toxoid or CRM. Other suitable carrier proteins include inactivated bacterial toxins such as cholera toxoid (e.g., as described in Int'l Patent Application No. WO 2004/083251), *E. coli* LT, *E. coli* ST, and exotoxin A from Pseudomonas aeruginosa. Bacterial outer membrane proteins such as outer membrane complex c (OMPC), porins, transferrin binding proteins, pneumolysin, pneumococcal surface protein A (PspA), pneumococcal adhesion protein (PsaA) or *Haemophilus influenzae* protein D can also be used. Other proteins, such as ovalbumin, keyhole limpet hemocyanin (KLH), bovine serum albumin (BSA) or purified protein derivative of tuberculin (PPD) also can be used as carrier proteins.

As discussed previously herein, the number of lysine residues in the carrier protein that become conjugated to the saccharide can be characterized as a range of conjugated lysines. For example, in a given immunogenic composition, the $CRM_{197}$ may comprise 1 to 15 lysine residues out of 39 covalently linked to the saccharide. Another way to express this parameter is that about 2.5% to about 40% of $CRM_{197}$ lysines are covalently linked to the saccharide. For example, in a given immunogenic composition, the $CRM_{197}$ may comprise 1 to 20 lysine residues out of 39 covalently linked to the saccharide. Another way to express this parameter is that about 2.5% to about 50% of $CRM_{197}$ lysines are covalently linked to the saccharide.

Methods for Making Glycoconjugates

In order to make a glycoconjugate, a polysaccharide must first be activated (i.e. chemically modified) before it can be chemically linked to a carrier, such as a protein. Prior to the activation step, saccharides can be hydrolyzed or mechanically sized by pressure homogenization to achieve appropriate molecular weights (e.g. 50 kDa to 500 kDa) for activation and subsequent conjugation. Partial oxidation of carbohydrates in polysaccharides has been effectively utilized to generate aldehyde groups which are then coupled to amine groups, such as the lysine residues of carrier proteins, to generate immunogenic conjugates. It is important that the method used to conjugate a polysaccharide to a carrier protein results in a stable covalent linkage, and the reaction conditions are mild enough to maintain the structural integrity of the individual components. Methods commonly used to activate and couple polysaccharides to carrier proteins include reductive amination chemistry (RAC), cyanylation, and use of carbodiimide. Reductive amination typically involves the use of sodium or potassium periodate or periodic acid in order to selectively oxidize vicinal —OH groups into active aldehyde groups. Cyanylation is used to randomly convert —OH groups into active —CN groups. Carbodiimide is used to activate carboxyl groups by replacing —OH groups with carbodiimide.

Reductive amination chemistry (RAC) is one of the most common methods used to couple polysaccharides to proteins since the reaction between the resulting carbonyl group of the polysaccharide and the amino group of the carrier protein can form corresponding Schiffs' base, which can then be selectively reduced in the presence of sodium cyanoborohydride (NaCNBH$_3$) to a very stable saturated carbon-nitrogen bond. Furthermore, reductive amination can be carried out in aqueous solution under conditions mild enough to preserve the structural integrity of the saccharide and protein components. Following conjugation, unreacted aldehydes can then be capped via sodium borohydride (NaBH$_4$) reduction. The conjugate can then be purified (e.g., by ultrafiltration/diafiltration), giving a final bulk glycoconjugate in succinate buffered saline.

However, depending on the particular polysaccharide, use of the common methods noted above does not always provide adequate results. For example, direct oxidation of polysaccharides with sodium periodate can result in result in the cleavage of the polysaccharide backbone.

For example, it was observed that for the conjugates prepared using standard periodate oxidation conditions (followed by reductive amination), representative batches showed an increase in free polysaccharide and a reduction in molecular weight, at 25° C. and above. The present disclosure provides the finding that the use of an N-oxoammonium salt based oxidation method resulted in improved stability of several *S. pneumoniae* polysaccharide conjugates, particularly Serotype 12F. In particular, as shown in further detail in Examples 1 to 7, the free radical 2,2,6,6,-Tetramethyl piperidinyloxy (TEMPO) was used in combination with N-chlorosuccinimide (NCS) to effectively oxidize the primary hydroxyl groups of Serotypes 12F, 10A, 3 and 33F in order to improve the stability of the resulting conjugates. Although selective oxidation of primary alcohols to aldehydes using TEMPO/NCS has been shown in the context of organic chemical reactions using small molecules in organic solvents (see, e.g. Einhorn et al., *J. Org. Chem.* 61, pp. 7452-7454 (1996)), the present disclosure provides the novel finding that TEMPO/NCS can be used as an oxidizing agent to selectively oxidize complex polysaccharides in aqueous solution in order to produce stable polysaccharide protein conjugates.

Accordingly, in one embodiment, the present disclosure provides methods of making glycoconjugates that comprise a saccharide conjugated to a carrier protein, comprising the steps of: a) reacting a saccharide with a stable nitroxyl radical compound and an oxidant to produce an activated saccharide; and b) reacting the activated saccharide with a carrier protein comprising one or more amine groups.

In an aspect, the unreacted aldehyde groups are converted back to primary alcohols during a capping step, using borohydride, after conjugation with the carrier protein, therefore minimizing the saccharide epitope modification during the modification steps involving oxidation followed by conjugation.

In an aspect, step a) of the reaction is carried out in aqueous solvent. In another aspect, step a) is carried out in aprotic solvent. In an aspect, step a) is carried out in DMSO (dimethylsulfoxide), Dimethylacetamide (DMA), Sulfolane, N-Methyl-2-pyrrolidone (NMP), Hexamethylphosphoramide (HMPA) or in DMF (dimethylformamide) solvent.

In an aspect, said stable nitroxyl radical compound are piperidine-N-oxy or pyrrolidine-N-oxy compounds. Preferably said compounds have the ability to selectively oxidize primary alcohols in the presence of an oxidant, to generate aldehyde groups, without affecting secondary hydroxyl groups. More preferably, said compounds have the ability to selectively oxidize primary alcohol in the presence of an oxidant, to generate aldehyde groups, without over oxidation to carboxyl groups. In an embodiment, said stable nitroxyl radical compound is a molecule bearing a TEMPO or a PROXYL (2,2,5,5-tetramethyl-1-pyrrolidinyloxy) moiety. Preferably said molecule has the ability to selectively oxidize primary alcohol in the presence of an oxidant, to generate aldehyde groups, without affecting secondary hydroxyl groups. More preferably said molecule has the ability to selectively oxidize primary alcohols in the presence of an oxidant, to generate aldehyde groups, without over oxidation to carboxyl groups. In an aspect, said stable nitroxyl radical compound is TEMPO or a derivative thereof. In an embodiment, said stable nitroxyl radical compound is selected from the groups consisting of TEMPO, 2,2,6,6-Tetramethyl-4-(methylsulfonyloxy)-1-piperidinooxy, 4-Phosphonooxy-TEMPO, 4-Oxo-TEMPO, 4-Methoxy-TEMPO, 4-Isothiocyanato-TEMPO, 4-(2-Iodoacetamido)-TEMPO free radical, 4-Hydroxy-TEMPO, 4-Cyano-TEMPO, 4-Carboxy-TEMPO, 4-(2-Bromoacetamido)-TEMPO, 4-Amino-TEMPO, 4-Acetamido-2,2,6,6-tetramethylpiperidine 1-oxyl. Preferably said stable nitroxyl radical compound is TEMPO. In a further embodiment, said stable nitroxyl radical compound is selected from the groups consisting of 3β-DOXYL-5α-cholestane, 5-DOXYL-stearic acid, 16-DOXYL-stearic acid, Methyl 5-DOXYL-stearate, 3-(Aminomethyl)-PROXYL, 3-Carbamoyl-PROXYL, 3-Carbamoyl-2,2,5,5-tetramethyl-3-pyrrolin-1-oxyl, 3-Carboxy-PROXYL, 3-Cyano-PROXYL. In an embodiment, said oxidant is a molecule bearing a N-halo moiety. Preferably said molecule has the ability to selectively oxidize primary alcohol in the presence of a nitroxyl radical compound. In an embodiment, said oxidant is selected from the group consisting of N-Chlorosuccinimide, N-Bromosuccinimide, N-Iodosuccinimide, Dichloroisocyanuric acid, 1,3,5-trichloro-1,3,5-triazinane-2,4,6-trione, Dibromoisocyanuric acid, 1,3,5-tribromo-1,3,5-triazinane-2,4,6-trione, Diiodoisocyanuric acid and 1,3,5-triiodo-1,3,5-triazinane-2,4,6-trione. Preferably said oxidant is N-Chlorosuccinimide.

In an aspect, the saccharide is reacted with 0.1 to 10 molar equivalent of oxidant. Preferably, the saccharide is reacted with 0.2 to 5, 0.5 to 2.5 or 0.5 to 1.5 molar equivalent of oxidant. In an aspect, the polysaccharide is reacted with about 0.2, 0.4, 0.6, 0.8, 1, 1.2, 1.4, 1.6, 1.8, 2, 2.2, 2.4, 2.6, 2.8, 3, 3.2, 3.4, 3.6, 3.8, 4, 4.2, 4.4, 4.6, 4.8 or 5 molar equivalent of oxidant.

In an aspect, the stable nitroxyl radical compound is present in a catalytic amount. In an aspect, the saccharide is reacted with less than about 0.3 molar equivalent of stable nitroxyl radical compound. In an aspect, the saccharide is reacted with less than about 0.005 molar equivalent of stable nitroxyl radical compound. In an aspect, the saccharide is reacted with about 0.005, 0.01, 0.05 or 0.1 molar equivalent of stable nitroxyl radical compound.

In one embodiment, the present disclosure provides methods of making glycoconjugates that comprise a saccharide conjugated to a carrier protein, comprising the steps of: a) reacting a saccharide with 2,2,6,6-tetramethyl-1-piperidinyloxy (TEMPO) and N-chlorosuccinimide (NCS) in an aqueous solvent to produce an activated saccharide; and b) reacting the activated saccharide with a carrier protein comprising one or more amine groups.

In other embodiments, the method further comprises a step of purifying the glycoconjugate, for example, by diafiltration.

In each case, the saccharide is selected from the group consisting of a polysaccharide, an oligosaccharide and a monosaccharide.

In each case, the said saccharide may be purified from the fermentation medium or synthetically derived.

In frequent embodiments, the carrier protein is $CRM_{197}$. In one embodiment, the bacterial capsular polysaccharide is a capsular polysaccharide derived from *S. pneumoniae*. In another preferred embodiment, the bacterial capsular polysaccharide is a capsular polysaccharide derived from *N. meningitides*.

In one embodiment the method of producing a glycoconjugate of the disclosure comprises the step of isolating the saccharide-carrier protein conjugate after it is produced. In frequent embodiments, the glycoconjugate is isolated by ultra-filtration.

In one embodiment, the carrier protein used in the method of producing an isolated *S. pneumoniae* capsular polysaccharide-carrier protein conjugate comprises $CRM_{197}$. In one embodiment, the carrier protein used in the method of producing an isolated *N. meningitidis* capsular polysaccharide-carrier protein conjugate comprises $CRM_{197}$.

In one embodiment, the $CRM_{197}$ is reacted with the activated polysaccharide at a ratio by weight of about 1:1.

In one embodiment, the method of producing an isolated *S. pneumoniae* capsular polysaccharide:carrier protein conjugate comprises the step of capping the polysaccharide-carrier protein conjugate reaction mixture to remove unreacted activation groups.

In one embodiment, the $CRM_{197}$ in the method of producing capsular polysaccharide-$CRM_{197}$ conjugate is added in a ratio by weight of about 0.4:1 $CRM_{197}$:capsular polysaccharide molecule. In other embodiments, the ratio by weight of $CRM_{197}$:capsular polysaccharide is about 0.5:1, about 0.6:1, about 0.7:1, about 0.8:1, about 0.9:1, about 1:1, about 1.1:1, about 1.2:1, about 1.3:1, about 1.4:1, or about 1.5:1.

In one embodiment, the saccharide used in the method of producing the glycoconjugate of the disclosure has a molecular weight between about 10 kDa and about 2,000 kDa. In other embodiments, the molecular weight is between about 50 kDa and about 1,000 kDa, between about 50 kDa and about 20,000 kDa, between about 200 kDa and about 10,000 kDa, between about 1,000 kDa and about 3,000 kDa.

In another aspect, the disclosure provides an immunogenic composition comprising a glycoconjugate produced by any of the methods described herein.

In another aspect, the disclosure provides an immunogenic composition comprising a glycoconjugate obtainable by any of the methods described herein.

Immunogenic Compositions

The term "immunogenic composition" relates to any pharmaceutical composition containing an antigen, e.g., a microorganism or a component thereof, which composition can be used to elicit an immune response in a subject.

As used herein, "immunogenic" means an ability of an antigen (or an epitope of the antigen), such as a bacterial capsular polysaccharide, or a glycoconjugate or immunogenic composition comprising the antigen, to elicit an immune response in a host such as a mammal, either humorally or cellularly mediated, or both.

Accordingly, a "glycoconjugate" or "conjugate" as used herein means any glycoconjugate containing an antigen or antigenic determinant (i.e., epitope) of a bacterial capsular polysaccharide conjugated to a carrier molecule that can be used to elicit an immune response.

The glycoconjugate may serve to sensitize the host by the presentation of the antigen in association with MHC molecules at a cell surface. In addition, antigen-specific T-cells or antibodies can be generated to allow for the future protection of an immunized host. Glycoconjugates thus can protect the host from one or more symptoms associated with infection by the bacteria, or may protect the host from death due to the infection with the bacteria associated with the capsular polysaccharide. Glycoconjugates may also be used to generate polyclonal or monoclonal antibodies, which may be used to confer passive immunity to a subject. Glycoconjugates may also be used to generate antibodies that are functional as measured by the killing of bacteria in either an animal efficacy model or via an opsonophagocytic killing assay.

An "antibody" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, unless otherwise indicated by context, the term is intended to encompass not only intact polyclonal or monoclonal antibodies, but also engineered antibodies (e.g., chimeric, humanized and/or derivatized to alter effector functions, stability and other biological activities) and fragments thereof (such as Fab, Fab', F(ab')2, Fv), single chain (ScFv) and domain antibodies, including shark and camelid antibodies), and fusion proteins comprising an antibody portion, multivalent antibodies, multispecific antibodies (e.g., bispecific antibodies so long as they exhibit the desired biological activity) and antibody fragments as described herein, and any other modified configuration of the immunoglobulin molecule that comprises an antigen recognition site. An antibody includes an antibody of any class, such as IgG, IgA, or IgM (or sub-class thereof), and the antibody need not be of any particular class. Depending on the antibody amino acid sequence of the constant domain of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2 in humans. The heavy-chain constant domains that correspond to the different classes of immunoglobulins are called alpha, delta, epsilon, gamma, and mu, respectively. The subunit structures and three-dimensional configurations of different classes of immunoglobulins are well known.

"Antibody fragments" comprise only a portion of an intact antibody, wherein the portion preferably retains at least one, preferably most or all, of the functions normally associated with that portion when present in an intact antibody.

The term "antigen" generally refers to a biological molecule, usually a protein, peptide, polysaccharide or conjugate in an immunogenic composition, or immunogenic substance that can stimulate the production of antibodies or T-cell responses, or both, in an animal, including compositions that are injected or absorbed into an animal. The immune response may be generated to the whole molecule, or to a various portions of the molecule (e.g., an epitope or hapten). The term may be used to refer to an individual molecule or to a homogeneous or heterogeneous population of antigenic molecules. An antigen is recognized by antibodies, T-cell receptors or other elements of specific humoral and/or cellular immunity. "Antigen" also includes all related antigenic epitopes. Epitopes of a given antigen can be identified using any number of epitope mapping techniques, well known in the art. See, e.g., Epitope Mapping Protocols in Methods in Molecular Biology, Vol. 66 (Glenn E. Morris, Ed., 1996) Humana Press, Totowa, N. J. For example, linear epitopes may be determined by, e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al. (1984) *Proc. Natl. Acad. Sci. USA* 81:3998-4002; Geysen et al. (1986) *Molec. Immunol.* 23:709-715; each of which is incorporated herein by reference as if set forth in its entirety. Similarly, conformational epitopes may be identified by determining spatial conformation of amino acids such as by, e.g., x-ray crystallography and 2-dimensional nuclear magnetic resonance. See, e.g., Epitope Mapping Protocols, supra.

Furthermore, for purposes of the present disclosure, "antigen" also can be used to refer to a protein that includes modifications, such as deletions, additions and substitutions (generally conservative in nature, but they may be non-conservative), to the native sequence, as long as the protein maintains the ability to elicit an immunological response. These modifications may be deliberate, as through site-directed mutagenesis, or through particular synthetic procedures, or through a genetic engineering approach, or may be accidental, such as through mutations of hosts, which produce the antigens. Furthermore, the antigen can be derived, obtained, or isolated from a microbe, e.g., a bacterium, or can be a whole organism. Similarly, an oligonucleotide or polynucleotide, which expresses an antigen, such as in nucleic acid immunization applications, is also included in the definition. Synthetic antigens are also included, e.g., polyepitopes, flanking epitopes, and other recombinant or synthetically derived antigens (Bergmann et al. (1993) *Eur. J. Immunol.* 23:2777 2781; Bergmann et al. (1996) *J. Immunol.* 157:3242-3249; Suhrbier (1997) *Immunol. Cell Biol.* 75:402 408; Gardner et al. (1998) 12th World AIDS Conference, Geneva, Switzerland, Jun. 28 to Jul. 3, 1998).

A "protective" immune response refers to the ability of an immunogenic composition to elicit an immune response, either humoral or cell mediated, or both, which serves to protect a subject from an infection. The protection provided need not be absolute, i.e., the infection need not be totally prevented or eradicated, if there is a statistically significant improvement compared with a control population of subjects, e.g. infected animals not administered the vaccine or immunogenic composition. Protection may be limited to mitigating the severity or rapidity of onset of symptoms of the infection. In general, a "protective immune response" would include the induction of an increase in antibody levels specific for a particular antigen in at least 50% of subjects, including some level of measurable functional antibody responses to each antigen. In particular situations, a "protective immune response" could include the induction of a two fold increase in antibody levels or a fourfold increase in antibody levels specific for a particular antigen in at least 50% of subjects, including some level of measurable functional antibody responses to each antigen. In certain embodiments, opsonising antibodies correlate with a protective immune response. Thus, protective immune response may be assayed by measuring the percent decrease in the bacterial count in an opsonophagocytosis assay, for instance those described below. Preferably, there is a decrease in bacterial count of at least 10%, 25%, 50%, 65%, 75%, 80%, 85%, 90%, 95% or more. The "immunogenic amount" of a particular conjugate in a composition is generally dosed based on total polysaccharide, conjugated and non-conjugated for that conjugate. For example, a capsular polysaccharide conjugate with 20% free polysaccharide will have about 80 mcg of conjugated polysaccharide and about 20 mcg of non-conjugated polysaccharide in a 100 mcg dose. The protein contribution to the conjugate is usually not considered when calculating the dose of a conjugate. Generally, each dose will comprise 0.1 to 100 mcg of polysaccharide, particularly 0.1 to 10 mcg, and more particularly 1 to 10 mcg.

One embodiment of the disclosure provides an immunogenic composition comprising any of the glycoconjugates comprising a *S. pneumoniae* capsular polysaccharide conjugated to a carrier protein described above.

The immunogenic compositions of the present disclosure can be used to protect or treat a human susceptible to bacterial infection, e.g., by a *S. pneumoniae* bacteria or a *N. meningitidis* bacteria, by means of administering the immunogenic compositions via a systemic, dermal or mucosal route, or can be used to generate a polyclonal or monoclonal antibody preparation that could be used to confer passive immunity on another subject. These administrations can include injection via the intramuscular, intraperitoneal, intradermal or subcutaneous routes; or via mucosal administration to the oral/alimentary, respiratory or genitourinary tracts. Immunogenic compositions may also be used to generate antibodies that are functional as measured by the killing of bacteria in either an animal efficacy model or via an opsonophagocytic killing assay.

Optimal amounts of components for a particular immunogenic composition can be ascertained by standard studies involving observation of appropriate immune responses in subjects. Following an initial vaccination, subjects can receive one or several booster immunizations adequately spaced.

In one embodiment, the immunogenic compositions of the disclosure further comprise at least one of an adjuvant, a buffer, a cryoprotectant, a salt, a divalent cation, a non-ionic detergent, an inhibitor of free radical oxidation, a diluent or a carrier. In one embodiment, the adjuvant within the immunogenic composition of the disclosure is an aluminum-based adjuvant. In one embodiment, the adjuvant is an aluminum-based adjuvant selected from the group consisting of aluminum phosphate, aluminum sulfate and aluminum hydroxide. In one embodiment, the adjuvant is aluminum phosphate.

An adjuvant is a substance that enhances the immune response when administered together with an immunogen or antigen. A number of cytokines or lymphokines have been shown to have immune modulating activity, and thus may be useful in a manner the same or similar to adjuvants, including, but not limited to, the interleukins 1-α, 1-β, 2, 4, 5, 6, 7, 8, 10, 12 (see, e.g., U.S. Pat. No. 5,723,127), 13, 14, 15, 16, 17 and 18 (and its mutant forms); the interferons-α, β and γ; granulocyte-macrophage colony stimulating factor (GM-CSF) (see, e.g., U.S. Pat. No. 5,078,996 and ATCC Accession Number 39900); macrophage colony stimulating factor (M-CSF), granulocyte colony stimulating factor (G-CSF), and the tumor necrosis factors α and β. Still other adjuvants that are useful with the immunogenic compositions described herein include chemokines, including without limitation, MCP-1, MIP-1α, MIP-1β, and RANTES; adhesion molecules, such as a selectin, e.g., L-selectin, P-selectin and E-selectin; mucin-like molecules, e.g., CD34, GlyCAM-1 and MadCAM-1, a member of the integrin family such as LFA-1, VLA-1, Mac-1 and p150.95; a member of the immunoglobulin superfamily such as PECAM, (CAMs, e.g., ICAM-1, ICAM-2 and ICAM-3, CD2 and LFA-3; co-stimulatory molecules such as B7-1, B7-2, CD40 and CD40L, growth factors including vascular growth factor, nerve growth factor, fibroblast growth factor, epidermal growth factor, PDGF, BL-1, and vascular endothelial growth factor; receptor molecules including Fas, TNF receptor, Flt, Apo-1, p55, WSL-1, DR3, TRAMP, Apo-3, AIR, LARD, NGRF, DR4, DR5, KILLER, TRAIL-R2, TRICK2, and DR6; and Caspases, including ICE.

Suitable adjuvants used to enhance an immune response may further include, without limitation, MPL™ (3-O-deacylated monophosphoryl lipid A, Corixa; Hamilton, MT), which is described in U.S. Pat. No. 4,912,094. Also suitable for use as adjuvants are synthetic lipid A analogs or aminoalkyl glucosamine phosphate compounds (AGP), or derivatives or analogs thereof, which are available from Corixa, and those that are described in U.S. Pat. No. 6,113,918. One such AGP is 2-[(R)-3-Tetradecanoyloxytetradecanoylamino] ethyl 2-Deoxy-4-O-phosphono-3-O-[(R)-3-tetradecanoyoxytetradecanoyl]-2-[(R)-3-tetradecanoyloxytetradecanoyl-amino]-b-D-glucopyranoside, which is also known as 529 (formerly known as RC529). This 529 adjuvant is formulated as an aqueous form (AF) or as a stable emulsion (SE).

Still other adjuvants include muramyl peptides, such as N-acetyl-muramyl-L-threonyl- D-isoglutamine (thr-MDP), N-acetyl-normuramyl-L-alanine- 2-(1'-2' dipalmitoyl-sn-glycero-3-hydroxyphosphoryloxy)-ethylamine (MTP-PE); oil-in-water emulsions, such as MF59 (U.S. Pat. No. 6,299,884) (containing 5% Squalene, 0.5% polysorbate 80, and 0.5% Span 85 (optionally containing various amounts of MTP-PE) formulated into submicron particles using a microfluidizer such as Model 110Y microfluidizer (Microfluidics, Newton, MA)), and SAF (containing 10% Squalene, 0.4% polysorbate 80, 5% pluronic-blocked polymer L121, and thr-MDP, either microfluidized into a submicron emulsion or vortexed to generate a larger particle size emulsion); incomplete Freund's adjuvant (IFA); aluminum salts (alum), such as aluminum hydroxide, aluminum phosphate, aluminum sulfate; Amphigen; Avridine; L121/squalene; D-lactide-polylactide/glycoside; pluronic polyols; killed Bordetella; saponins, such as STIMULON™ QS-21 (Antigenics, Framingham, MA), described in U.S. Pat. No. 5,057,540, ISCOMATRIX™ (CSL Limited, Parkville, Australia), described in U.S. Pat. No. 5,254,339, and immunostimulating complexes (ISCOMS); *Mycobacterium tuberculosis*; bacterial lipopolysaccharides; synthetic polynucleotides such as oligonucleotides containing a CpG motif (e.g., U.S. Pat. No. 6,207,646); IC-31 (Intercell AG, Vienna, Austria), described in EP Patent Nos. 1,296,713 and 1,326,634; a pertussis toxin (PT) or mutant thereof, a cholera toxin or mutant thereof (e.g., U.S. Pat. Nos. 7,285,281, 7,332,174, 7,361,355 and 7,384,640); or an *E. coli* heat-labile toxin (LT) or mutant thereof, particularly LT-K63, LT-R72 (e.g., U.S. Pat. Nos. 6,149,919, 7,115,730 and 7,291,588).

The immunogenic composition optionally can comprise a pharmaceutically acceptable carrier. Pharmaceutically acceptable carriers include carriers approved by a regulatory agency of a Federal, a state government, or other regulatory agency, or listed in the U.S. Pharmacopeia or other generally recognized pharmacopeia for use in animals, including humans as well as non-human mammals. The term carrier may be used to refer to a diluent, adjuvant, excipient, or vehicle with which the pharmaceutical composition is administered. Water, saline solutions and aqueous dextrose and glycerol solutions can be employed as liquid carriers, particularly for injectable solutions. Examples of suitable pharmaceutical carriers are described in "Remington's Pharmaceutical Sciences" by E. W. Martin. The formulation should suit the mode of administration.

The immunogenic compositions of the present disclosure can further comprise one or more additional immunomodulators, which are agents that perturb or alter the immune system, such that either up-regulation or down-regulation of humoral and/or cell-mediated immunity is observed. In one embodiment, up-regulation of the humoral and/or cell-mediated arms of the immune system is provided.

Examples of certain immunomodulators include, e.g., an adjuvant or cytokine, or ISCOMATRIX™ (CSL Limited; Parkville, Australia), described in U.S. Pat. No. 5,254,339 among others. Non-limiting examples of adjuvants that can be used in the immunogenic composition of the present disclosure include the R1131 adjuvant system (Ribi Inc.; Hamilton, MT), alum, mineral gels such as aluminum hydroxide gel, oil-in-water emulsions, water-in-oil emulsions such as, e.g., Freund's complete and incomplete adjuvants, Block copolymer (CytRx; Atlanta, GA), QS-21 (Cambridge Biotech Inc.; Cambridge, MA), SAF-M (Chiron; Emeryville, CA), AMPHIGEN™ adjuvant, saponin, Quil A or other saponin fraction, monophosphoryl lipid A, and avridine (N,N-Dioctadecyl-N',N'-bis(2-hydroxyethyl)-1,3-diaminopropane, N, N-Dioctadecyl-N',N'-bis(2-hydroxyethyl)propanediamine) lipid-amine adjuvant. Non-limiting examples of oil-in-water emulsions useful in the immunogenic composition of the disclosure include modified SEAM62 and SEAM ½ formulations. Modified SEAM62 is an oil-in-water emulsion containing 5% (v/v) squalene (Sigma), 1% (v/v) SPAN™ 85 detergent (ICI Surfactants), 0.7% (v/v) polysorbate 80 detergent (ICI Surfactants), 2.5% (v/v) ethanol, 200 mcg/mL Quil A, 100 mcg/ml cholesterol, and 0.5% (v/v) lecithin. Modified SEAM ½ is an oil-in-water emulsion comprising 5% (v/v) squalene, 1% (v/v) SPAN™ 85 detergent, 0.7% (v/v) polysorbate 80 detergent, 2.5% (v/v) ethanol, 100 mcg/ml Quil A, and 50 mcg/ml cholesterol. Other immunomodulators that can be included in the immunogenic composition include, e.g., one or more interleukins, interferons, or other known cytokines or chemokines. In one embodiment, the adjuvant may be a cyclodextrin derivative or a polyanionic polymer, such as those described in U.S. Pat. Nos. 6,165,995 and 6,610,310, respectively. It is to be understood that the immunomodulator and/or adjuvant to be used will depend on the subject to which the immunogenic composition will be administered, the route of injection and the number of injections to be given.

The immunogenic compositions of the disclosure may further comprise one or more preservatives in addition to a plurality of capsular polysaccharide-protein conjugates. The FDA requires that biological products in multiple-dose (multi-dose) vials contain a preservative, with only a few exceptions. Vaccine products containing preservatives include vaccines containing benzethonium chloride (anthrax), 2-phenoxyethanol (DTaP, HepA, Lyme, Polio (parenteral)), phenol (Pneumo, Typhoid (parenteral), Vaccinia) and thimerosal (DTaP, DT, Td, HepB, Hib, Influenza, JE, Mening, Pneumo, Rabies). Preservatives approved for use in injectable drugs include, e.g., chlorobutanol, m-cresol, methylparaben, propylparaben, 2-phenoxyethanol, benzethonium chloride, benzalkonium chloride, benzoic acid, benzyl alcohol, phenol, thimerosal and phenylmercuric nitrate.

Packaging and Dosing Forms

Formulations of the disclosure may further comprise one or more of a buffer, a salt, a divalent cation, a non-ionic detergent, a cryoprotectant such as a sugar, and an antioxidant such as a free radical scavenger or chelating agent, or any multiple combination thereof. The choice of any one component, e.g., a chelator, may determine whether or not another component (e.g., a scavenger) is desirable. The final composition formulated for administration should be sterile and/or pyrogen free. The skilled artisan may empirically determine which combinations of these and other components will be optimal for inclusion in the preservative containing immunogenic compositions of the disclosure depending on a variety of factors such as the particular storage and administration conditions required.

In certain embodiments, a formulation of the disclosure which is compatible with parenteral administration comprises one or more physiologically acceptable buffers selected from, but not limited to, Tris (trimethamine), phosphate, acetate, borate, citrate, glycine, histidine and succinate. In certain embodiments, the formulation is buffered to within a pH range of about 6.0 to about 9.0, preferably from about 6.4 to about 7.4.

In certain embodiments, it may be desirable to adjust the pH of the immunogenic composition or formulation of the disclosure. The pH of a formulation of the disclosure may be adjusted using standard techniques in the art. The pH of the formulation may be adjusted to be between 3.0 and 8.0. In certain embodiments, the pH of the formulation may be, or may adjusted to be, between 3.0 and 6.0, 4.0 and 6.0, or 5.0 and 8.0. In other embodiments, the pH of the formulation may be, or may adjusted to be, about 3.0, about 3.5, about 4.0, about 4.5, about 5.0, about 5.5, about 5.8, about 6.0, about 6.5, about 7.0, about 7.5, or about 8.0. In certain embodiments, the pH may be, or may adjusted to be, in a range from 4.5 to 7.5, or from 4.5 to 6.5, from 5.0 to 5.4, from 5.4 to 5.5, from 5.5 to 5.6, from 5.6 to 5.7, from 5.7 to 5.8, from 5.8 to 5.9, from 5.9 to 6.0, from 6.0 to 6.1, from 6.1 to 6.2, from 6.2 to 6.3, from 6.3 to 6.5, from 6.5 to 7.0, from 7.0 to 7.5 or from 7.5 to 8.0. In a specific embodiment, the pH of the formulation is about 5.8.

In certain embodiments, a formulation of the disclosure which is compatible with parenteral administration comprises one or more divalent cations, including but not limited to $MgCl_2$, $CaCl_2$ and $MnCl_2$, at a concentration ranging from about 0.1 mM to about 10 mM, with up to about 5 mM being preferred.

In certain embodiments, a formulation of the disclosure which is compatible with parenteral administration comprises one or more salts, including but not limited to sodium chloride, potassium chloride, sodium sulfate, and potassium sulfate, present at an ionic strength which is physiologically acceptable to the subject upon parenteral administration and included at a final concentration to produce a selected ionic strength or osmolarity in the final formulation. The final ionic strength or osmolality of the formulation will be determined by multiple components (e.g., ions from buffering compound(s) and other non-buffering salts. A preferred salt, NaCl, is present from a range of up to about 250 mM, with salt concentrations being selected to complement other components (e.g., sugars) so that the final total osmolarity of the formulation is compatible with parenteral administration (e.g., intramuscular or subcutaneous injection) and will promote long term stability of the immunogenic components of the immunogenic composition formulation over various temperature ranges. Salt-free formulations will tolerate increased ranges of the one or more selected cryoprotectants to maintain desired final osmolarity levels.

In certain embodiments, a formulation of the disclosure which is compatible with parenteral administration comprises one or more cryoprotectants selected from but not limited to disaccharides (e.g., lactose, maltose, sucrose or trehalose) and polyhydroxy hydrocarbons (e.g., dulcitol, glycerol, mannitol and sorbitol).

In certain embodiments, the osmolarity of the formulation is in a range of from about 200 mOs/L to about 800 mOs/L, with a preferred range of from about 250 mOs/L to about 500 mOs/L, or about 300 mOs/L—about 400 mOs/L. A salt-free formulation may contain, for example, from about 5% to about 25% sucrose, and preferably from about 7% to about 15%, or about 10% to about 12% sucrose. Alternatively, a salt-free formulation may contain, for example, from about 3% to about 12% sorbitol, and preferably from about 4% to 7%, or about 5% to about 6% sorbitol. If salt such as sodium chloride is added, then the effective range of sucrose or sorbitol is relatively decreased. These and other such osmolality and osmolarity considerations are well within the skill of the art.

In certain embodiments, a formulation of the disclosure which is compatible with parenteral administration comprises one or more free radical oxidation inhibitors and/or chelating agents. A variety of free radical scavengers and chelators are known in the art and apply to the formulations and methods of use described herein. Examples include but are not limited to ethanol, EDTA, an EDTA/ethanol combination, triethanolamine, mannitol, histidine, glycerol, sodium citrate, inositol hexaphosphate, tripolyphosphate, ascorbic acid/ascorbate, succinic acid/succinate, malic acid/maleate, desferal, EDDHA and DTPA, and various combinations of two or more of the above. In certain embodiments, at least one non-reducing free radical scavenger may be added at a concentration that effectively enhances long term stability of the formulation. One or more free radical oxidation inhibitors/chelators may also be added in various combinations, such as a scavenger and a divalent cation. The choice of chelator will determine whether or not the addition of a scavenger is needed.

In certain embodiments, a formulation of the disclosure which is compatible with parenteral administration comprises one or more non-ionic surfactants, including but not limited to polyoxyethylene sorbitan fatty acid esters, polysorbate-80 (TWEEN™ 80), polysorbate-60 (TWEEN™ 60), polysorbate-40 (TWEEN™ 40) and polysorbate-20 (TWEEN™ 20), polyoxyethylene alkyl ethers, including but not limited to Brij 58, Brij 35, as well as others such as TRITON™ X-100; TRITON™ X-114, NP40 (nonyl phenoxypolyethoxylethanol), SPAN™ 85 and the PLURONIC™ series of non-ionic surfactants (e.g., PLURONIC™ 121), with preferred components polysorbate-80 at a concentration from about 0.001% to about 2% (with up to about 0.25% being preferred) or polysorbate-40 at a concentration from about 0.001% to 1% (with up to about 0.5% being preferred).

In certain embodiments, a formulation of the disclosure comprises one or more additional stabilizing agents suitable for parenteral administration, e.g., a reducing agent comprising at least one thiol (—SH) group (e.g., cysteine, N-acetyl cysteine, reduced glutathione, sodium thioglycolate, thiosulfate, monothioglycerol, or mixtures thereof). Alternatively or optionally, preservative-containing immunogenic composition formulations of the disclosure may be further stabilized by removing oxygen from storage containers, protecting the formulation from light (e.g., by using amber glass containers).

Preservative-containing immunogenic composition formulations of the disclosure may comprise one or more pharmaceutically acceptable carriers or excipients, which include any excipient that does not itself induce an immune response. Suitable excipients include but are not limited to macromolecules such as proteins, saccharides, polylactic acids, polyglycolic acids, polymeric amino acids, amino acid copolymers, sucrose (Paoletti et al, 2001, *Vaccine*, 19:2118), trehalose, lactose and lipid aggregates (such as oil droplets or liposomes). Such carriers are well known to the skilled artisan. Pharmaceutically acceptable excipients are discussed, e.g., in Gennaro, 2000, Remington: The Science and Practice of Pharmacy, 20$^{th}$ edition, ISBN:0683306472.

Compositions of the disclosure may be lyophilized or in aqueous form, i.e. solutions or suspensions. Liquid formulations may advantageously be administered directly from their packaged form and are thus ideal for injection without the need for reconstitution in aqueous medium as otherwise required for lyophilized compositions of the disclosure.

Direct delivery of immunogenic compositions of the present disclosure to a subject may be accomplished by parenteral administration (intramuscularly, intraperitoneally, intradermally, subcutaneously, intravenously, or to the interstitial space of a tissue); or by rectal, oral, vaginal, topical, transdermal, intranasal, ocular, aural, pulmonary or other mucosal administration. In a preferred embodiment, parenteral administration is by intramuscular injection, e.g., to the thigh or upper arm of the subject. Injection may be via a needle (e.g. a hypodermic needle), but needle free injection may alternatively be used. A typical intramuscular dose is 0.5 mL. Compositions of the disclosure may be prepared in various forms, e.g., for injection either as liquid solutions or suspensions. In certain embodiments, the composition may be prepared as a powder or spray for pulmonary administration, e.g. in an inhaler. In other embodiments, the composition may be prepared as a suppository or pessary, or for nasal, aural or ocular administration, e.g. as a spray, drops, gel or powder. Optimal amounts of components for a particular immunogenic composition may be ascertained by standard studies involving observation of appropriate immune responses in subjects. Following an initial vaccination, subjects can receive one or several booster immunizations adequately spaced.

Immunogenic compositions of the disclosure may be packaged in unit dose or multi-dose form (e.g. 2 doses, 4 doses, or more). For multi-dose forms, vials are typically but not necessarily preferred over pre-filled syringes. Suitable multi-dose formats include but are not limited to: 2 to 10 doses per container at 0.1 to 2 mL per dose. In certain embodiments, the dose is a 0.5 mL dose. See, e.g., International Patent Application WO2007/127668, which is incorporated by reference herein.

Compositions may be presented in vials or other suitable storage containers, or may be presented in pre-filled delivery devices, e.g., single or multiple component syringes, which may be supplied with or without needles. A syringe typically but need not necessarily contains a single dose of the preservative-containing immunogenic composition of the disclosure, although multi-dose, pre-filled syringes are also envisioned. Likewise, a vial may include a single dose but may alternatively include multiple doses.

Effective dosage volumes can be routinely established, but a typical dose of the composition for injection has a volume of 0.5 mL. In certain embodiments, the dose is formulated for administration to a human subject. In certain embodiments, the dose is formulated for administration to an adult, teen, adolescent, toddler or infant (i.e., no more than one year old) human subject and may in preferred embodiments be administered by injection.

Liquid immunogenic compositions of the disclosure are also suitable for reconstituting other immunogenic compositions which are presented in lyophilized form. Where an immunogenic composition is to be used for such extemporaneous reconstitution, the disclosure provides a kit with two or more vials, two or more ready-filled syringes, or one or more of each, with the contents of the syringe being used to reconstitute the contents of the vial prior to injection, or vice versa.

Alternatively, immunogenic compositions of the present disclosure may be lyophilized and reconstituted, e.g., using one of a multitude of methods for freeze drying well known in the art to form dry, regular shaped (e.g., spherical) particles, such as micropellets or microspheres, having particle characteristics such as mean diameter sizes that may be selected and controlled by varying the exact methods used to prepare them. The immunogenic compositions may further comprise an adjuvant which may optionally be prepared with or contained in separate dry, regular shaped (e.g., spherical) particles such as micropellets or microspheres. In such embodiments, the present disclosure further provides an immunogenic composition kit comprising a first component that includes a stabilized, dry immunogenic composition, optionally further comprising one or more preservatives of the disclosure, and a second component comprising a sterile, aqueous solution for reconstitution of the first component. In certain embodiments, the aqueous solution comprises one or more preservatives, and may optionally comprise at least one adjuvant (see, e.g., WO2009/109550 (incorporated herein by reference)).

In yet another embodiment, a container of the multi-dose format is selected from one or more of the group consisting of, but not limited to, general laboratory glassware, flasks, beakers, graduated cylinders, fermentors, bioreactors, tubings, pipes, bags, jars, vials, vial closures (e.g., a rubber stopper, a screw on cap), ampoules, syringes, dual or multi-chamber syringes, syringe stoppers, syringe plungers, rubber closures, plastic closures, glass closures, cartridges and disposable pens and the like. The container of the present disclosure is not limited by material of manufacture, and includes materials such as glass, metals (e.g., steel, stainless steel, aluminum, etc.) and polymers (e.g., thermoplastics, elastomers, thermoplastic-elastomers). In a particular embodiment, the container of the format is a 5 mL Schott Type 1 glass vial with a butyl stopper. The skilled artisan will appreciate that the format set forth above is by no means an exhaustive list, but merely serve as guidance to the artisan with respect to the variety of formats available for the present disclosure. Additional formats contemplated for use in the present disclosure may be found in published catalogues from laboratory equipment vendors and manufacturers such as United States Plastic Corp. (Lima, OH), VWR.

Methods for Inducing an Immune Response and Protecting Against Infection

The present disclosure also includes methods of use for immunogenic compositions described herein. For example, one embodiment of the disclosure provides a method of inducing an immune response against a pathogenic bacteria, for example *S. pneumonia*, comprising administering to a subject an immunogenic amount of any of the immunogenic compositions described herein comprising a bacterial antigen such as a bacterial capsular polysaccharide derived from pathogenic bacteria. One embodiment of the disclosure provides a method of protecting a subject against an infection with *S. pneumoniae*, or a method of preventing infection with *S. pneumoniae*, or a method of reducing the severity of or delaying the onset of at least one symptom associated with an infection caused by *S. pneumoniae*, the methods comprising administering to a subject an immunogenic amount of any of the immunogenic compositions described herein comprising a bacterial antigen such as a bacterial capsular polysaccharide derived from *S. pneumoniae*. One embodiment of the disclosure provides a method of treating or preventing a Streptococcal infection, disease or condition associated with a *Streptococcus* sp. in a subject, the method comprising the step of administering a therapeutically or prophylactically effective amount of an immunogenic composition described herein to the subject. In some embodiments, the method of treating or preventing a Streptococcal infection, disease or conditions comprises human, veterinary, animal, or agricultural treatment. Another embodiment provides a method of treating or preventing a Streptococcal infection, disease or condition associated with a *Streptococcus* sp. in a subject, the method comprising generating a polyclonal or monoclonal antibody preparation from the immunogenic composition described herein, and using said antibody preparation to confer passive immunity to the subject. One embodiment of the disclosure provides a method of preventing a Streptococcal infection in a subject undergoing a surgical procedure, the method comprising the step of administering a prophylactically effective amount of an immunogenic composition described herein to the subject prior to the surgical procedure.

An "immune response" to an antigen or immunogenic composition is the development in a subject of a humoral and/or a cell-mediated immune response to molecules present in the antigen or vaccine composition of interest. For purposes of the present disclosure, a "humoral immune response" is an antibody-mediated immune response and involves the induction and generation of antibodies that recognize and bind with some affinity for the antigen in the immunogenic composition of the disclosure, while a "cell-mediated immune response" is one mediated by T-cells and/or other white blood cells. A "cell-mediated immune response" is elicited by the presentation of antigenic epitopes in association with Class I or Class II molecules of the major histocompatibility complex (MHC), CD1 or other non-classical MHC-like molecules. This activates antigen-specific CD4+ T helper cells or CD8+ cytotoxic T lymphocyte cells ("CTLs"). CTLs have specificity for peptide antigens that are presented in association with proteins encoded by classical or non-classical MHCs and expressed on the surfaces of cells. CTLs help induce and promote the intracellular destruction of intracellular microbes, or the lysis of cells infected with such microbes. Another aspect of cellular immunity involves an antigen-specific response by helper T-cells. Helper T-cells act to help stimulate the function, and focus the activity of, nonspecific effector cells against cells displaying peptide or other antigens in association with classical or non-classical MHC molecules on their surface. A "cell-mediated immune response" also refers to the production of cytokines, chemokines and other such molecules produced by activated T-cells and/or other white blood cells, including those derived from CD4+ and CD8+ T-cells. The ability of a particular antigen or composition to stimulate a cell-mediated immunological response may be determined by a number of assays, such as by lymphoproliferation (lymphocyte activation) assays, CTL cytotoxic cell assays, by assaying for T-lymphocytes specific for the antigen in a sensitized subject, or by measurement of cytokine production by T cells in response to re-stimulation with antigen. Such assays are well known in the art. See, e.g., Erickson et al. (1993) *J. Immunol.* 151:4189-4199; and Doe et al. (1994) *Eur. J. Immunol.* 24:2369-2376.

As used herein, "treatment" (including variations thereof, e.g., "treat" or "treated") means any one or more of the following: (i) the prevention of infection or re-infection, as in a traditional vaccine, (ii) the reduction in the severity of, or, in the elimination of symptoms, and (iii) the substantial or complete elimination of the pathogen or disorder in question. Hence, treatment may be effected prophylactically (prior to infection) or therapeutically (following infection). In the present disclosure, prophylactic treatment is the preferred mode. According to a particular embodiment of the present disclosure, compositions and methods are provided that treat, including prophylactically and/or therapeutically immunize, a host animal against a microbial infection (e.g., a bacterium such as Streptococcus). The methods of the present disclosure are useful for conferring prophylactic and/or therapeutic immunity to a subject. The methods of the present disclosure can also be practiced on subjects for biomedical research applications.

As used herein, "mammal" means a human or non-human animal. More particularly, mammal refers to any animal classified as a mammal, including humans, domestic and farm animals, and research, zoo, sports and pet companion animals such as a household pet and other domesticated animal including, but not limited to, cattle, sheep, ferrets, swine, horses, rabbits, goats, dogs, cats, and the like. Preferred companion animals are dogs and cats. Preferably, the mammal is human.

An "immunogenic amount," and "immunologically effective amount," both of which are used interchangeably herein, refers to the amount of antigen or immunogenic composition sufficient to elicit an immune response, either a cellular (T-cell) or humoral (B-cell or antibody) response, or both, as measured by standard assays known to one skilled in the art.

The amount of a particular conjugate in a composition is generally calculated based on total polysaccharide, conjugated and non-conjugated for that conjugate. For example, a conjugate with 20% free polysaccharide will have about 80 mcg of conjugated polysaccharide and about 20 mcg of non-conjugated polysaccharide in a 100 mcg polysaccharide dose. The protein contribution to the conjugate is usually not considered when calculating the dose of a conjugate. The amount of conjugate can vary depending upon the streptococcal serotype. Generally, each dose will comprise 0.1 to 100 mcg of polysaccharide, particularly 0.1 to 10 mcg, and more particularly 1 to 10 mcg. The "immunogenic amount" of the different polysaccharide components in the immunogenic composition, may diverge and each may comprise 1 mcg, 2 mcg, 3 mcg, 4 mcg, 5 mcg, 6 mcg, 7 mcg, 8 mcg, 9 mcg, 10 mcg, 15 mcg, 20 mcg, 30 mcg, 40 mcg, 50 mcg, 60 mcg, 70 mcg, 80 mcg, 90 mcg, or about 100 mcg of any particular polysaccharide antigen.

S. pneumoniae "invasive disease" is the isolation of bacteria from a normally sterile site, where there is associated clinical signs/symptoms of disease. Normally sterile body sites include blood, CSF, pleural fluid, pericardial fluid, peritoneal fluid, joint/synovial fluid, bone, internal body site (lymph node, brain, heart, liver, spleen, vitreous fluid, kidney, pancreas, ovary) or other normally sterile sites. Clinical conditions characterizing invasive diseases include bacteremia, pneumonia, cellulitis, osteomyelitis, endocarditis, septic shock and more.

The effectiveness of an antigen as an immunogen, can be measured either by proliferation assays, by cytolytic assays, such as chromium release assays to measure the ability of a T-cell to lyse its specific target cell, or by measuring the levels of B-cell activity by measuring the levels of circulating antibodies specific for the antigen in serum. An immune response may also be detected by measuring the serum levels of antigen specific antibody induced following administration of the antigen, and more specifically, by measuring the ability of the antibodies so induced to enhance the opsonophagocytic ability of particular white blood cells, as described herein. The level of protection of the immune response may be measured by challenging the immunized host with the antigen that has been administered. For example, if the antigen to which an immune response is desired is a bacterium, the level of protection induced by the immunogenic amount of the antigen is measured by detecting the percent survival or the percent mortality after challenge of the animals with the bacterial cells. In one embodiment, the amount of protection may be measured by measuring at least one symptom associated with the bacterial infection, e.g., a fever associated with the infection. The amount of each of the antigens in the multi-antigen or multi-component vaccine or immunogenic compositions will vary with respect to each of the other components and can be determined by methods known to the skilled artisan. Such methods would include procedures for measuring immunogenicity and/or in vivo efficacy. In certain embodiments, the term "about" means within 20%, preferably within 10%, and more preferably within 5% of the indicated value or range The disclosure further provides antibodies and antibody compositions which bind specifically and selectively to the capsular polysaccharides or glycoconjugates of the present disclosure. In some embodiments, antibodies are generated upon administration to a subject of the capsular polysaccharides or glycoconjugates of the present disclosure. In some embodiments, the disclosure provides purified or isolated antibodies directed against one or more of the capsular polysaccharides or glycoconjugates of the present disclosure. In some embodiments, the antibodies of the present disclosure are functional as measured by killing bacteria in either an animal efficacy model or via an opsonophagocytic killing assay. In some embodiments, the antibodies of the disclosure confer passive immunity to a subject. The present disclosure further provides polynucleotide molecules encoding an antibody or antibody fragment of the disclosure, and a cell, cell line (such as hybridoma cells or other engineered cell lines for recombinant production of antibodies) or a transgenic animal that produces an antibody or antibody composition of the disclosure, using techniques well-known to those of skill in the art.

Antibodies or antibody compositions of the disclosure may be used in a method of treating or preventing a Staphylococcal infection, disease or condition associated with a Streptococcus sp. in a subject, the method comprising generating a polyclonal or monoclonal antibody preparation, and using said antibody or antibody composition to confer passive immunity to the subject. Antibodies of the disclosure may also be useful for diagnostic methods, e.g., detecting the presence of or quantifying the levels of capsular polysaccharide or a glycoconjugate thereof.

The following examples are provided by way of illustration and not by way of limitation. Abbreviations: MW=molecular weight; WFI=water for injection; TEMPO=2,2,6,6-Tetramethyl-1-piperidinyloxy free radical; NCS=N-Chlorosuccinimide.

EXAMPLES

Example 1: Conjugation of Pn Serotype-12F Using TEMPO/NCS

In order to improve the stability of Serotype 12F-CRM$_{197}$ glycoconjugates, alternate chemistries were explored using 2,2,6,6-Tetramethyl-1-piperidinyloxy free radical (TEMPO) and N-Chlorosuccinimide (NCS) as the cooxidant to oxidize primary alcohols to aldehyde groups. GC/MS analysis showed that the sites of oxidation were different from that of periodate mediated oxidation. In the case of TEMPO-NCS oxidation, the α-D-Glcp and 2-Glcp were oxidized, whereas α-D-Galp was the major site of oxidation when periodate was used (see FIG. 1). As described in further detail herein, TEMPO was used in catalytic amounts 0.1 molar equivalents) and the desired degree of oxidation (DO) was achieved by varying the amounts of NCS used. Subsequently several conjugates were synthesized and characterized. In general, the production of Serotype 12F glycoconjugates was carried out in several phases, as follows:
1) Hydrolysis of Serotype 12 polysaccharide to molecular weights 50 to 500 kDa.
2) Activation of Serotype 12F polysaccharide with TEMPO/NCS
3) Purification of the activated polysaccharide
4) Conjugation of activated Serotype 12F to CRM$_{197}$ protein
5) Purification of Serotype 12F—CRM conjugates.

Example 2: Hydrolysis and Oxidation of Serotype 12F

The hydrolysis of the polysaccharide was typically performed under acidic conditions with heating to obtain an average molecular weight in the desired range of 100 to 350 kDa. A typical experiment is described below.
Hydrolysis
The Serotype 12F polysaccharide solution was added to a jacketed reaction vessel. To this, the required volume of 0.30 M Acetic acid and water for injection (WFI) were added to maintain ~0.1 M acetic acid concentration. The pH of the solution was adjusted to 3.2±0.3 using 1 N NaOH or Glacial Acetic acid. The temperature of the reaction mixture was increased to 70±5° C. The reaction mixture was stirred at 70±5° C. for 90-120 minutes. The reaction mixture was cooled down to 23±2° C. and neutralized (pH 7.0) by adding 1 M NaOH solution. The hydrolyzed polysaccharide was purified by ultrafiltration/diafiltration against WFI using 30K MWCO membranes. The solution was filtered through a 0.22 μm filter and stored at 2 to 8° C. until oxidation. The molecular weight of the hydrolyzed polysaccharide was analyzed by SEC-MALLS to ensure that the molecular weight met the target range of 100 to 350 kDa.

Partial Oxidation

In one experiment, the Serotype 12F polysaccharide was mechanically sized using pressure homogenization using a microfluidiser to reduce the molecular weight to approximately 100 to 500 kDa. The sized polysaccharide was added to a reaction vessel at a concentration of 4.0 mg/mL and mixed with bicarbonate/carbonate buffer (0.5 M $NaHCO_3$/ 0.05 M $Na_2CO_3$ buffer, pH 8.6) at a ratio of 1:1 v/v. To the stirred mixture was added 0.1 mol equivalent of TEMPO. The reaction was started by the addition of 0.6 to 1.0 mol equivalent of NCS. The reaction mixture was stirred at room temperature for 2 hours, after which the activated polysaccharide was purified by diafiltration, with WFI using a 30K ultrafiltration membrane. The purified polysaccharide was collected and the degree of oxidation (DO) was determined by quantitative measurements of aldehyde (using a 3-methyl-2-benothiazolinone hydrazone (MBTH) assay) and polysaccharide (using an anthrone assay).

In another experiment, the Serotype 12F polysaccharide was hydrolyzed to reduce the molecular weight to a molecular weight of approximately 100 to 500 kDa. The Serotype 12F polysaccharide was added to a reaction vessel and mixed with 0.5 M $NaHCO_3$/0.05 M $Na_2CO_3$ buffer (pH 8.6) at a ratio of 1:1 v/v. To the stirred mixture was added 0.6 to 1.0 molar equivalents of NCS dissolved in WFI. The activation was initiated by the addition of approximately 0.1 molar equivalents of TEMPO dissolved in WFI. The reaction mixture was stirred at room temperature for 2 hours, after which the activated polysaccharide was purified by diafiltration with WFI using a 30K ultra-filtration membrane. The purified activated polysaccharide was filtered through a 0.2 μm filter and stored at 4° C. before use.

The TEMPO/NCS mediated oxidations were also performed successfully in sodium phosphate buffers of pH 6.5, 7.0, 7.5 and 8.0. In some activation experiments a primary alcohol such as n-propanol was used to quench the reagents in order to avoid saccharide overoxidation. In another set of experiments the chemically hydrolysed polysaccharide was subjected to oxidation directly, without the ultrafiltration/ diafiltration purification step.

Example 3: Conjugation of Serotype 12F Oxidized Polysaccharide

In one experiment, the purified oxidized Serotype 12F polysaccharide was added to a reaction vessel followed by the addition of 0.5 M Sodium phosphate buffer (pH 6.5) to a final buffer concentration of 0.1 M. To this solution, previously lyophilized $CRM_{197}$ was added and mixed thoroughly in order to obtain a homogenous solution. The pH was adjusted to 6.8 using diluted HCl or 1N NaOH solution. This was followed by the addition of 1.5 molar equivalents of $NaCNBH_3$. The reaction mixture was stirred for 24 hours at room temperature (23° C.) and for 2.5 days at 37° C. The reaction mixture was then diluted with 1X 0.9% saline and the unreacted aldehyde groups were "capped" with 2 molar equivalents of sodium borohydride. The capping reaction time was 3 hours.

In another experiment, the purified activated Serotype 12F was added to a reaction vessel followed by the addition of 0.5 M sodium phosphate buffer (pH 6.5) to a final buffer concentration of 0.1 M. To this solution, previously lyophilized $CRM_{197}$ was added and mixed thoroughly to obtain a homogenous solution. The pH was adjusted to 6.8 using diluted HCl or 1N NaOH solution. This was followed by the addition of 3 molar equivalents of $NaCNBH_3$. The reaction mixture was stirred for 24 hours at 23° C. and for 48 hrs at 37° C. The reaction mixture was then diluted with 1X 0.9% saline and with stirring, the unreacted aldehyde groups were "capped" with 1 molar equivalent sodium borohydride $NaBH_4$. The capping reaction time was 3 hours.

In another experiment, the purified activated Serotype 12F was added to a reaction vessel and mixed with $CRM_{197}$ solution. The mixture was lyophilized and the powder was dissolved in 0.1 M sodium phosphate buffer (pH 6.8) to a final saccharide concentration of 5 mg/mL. If needed the pH was adjusted to 6.8 using diluted HCl or 1N NaOH solution. This was followed by the addition of 3 molar equivalents $NaCNBH_3$. The reaction mixture was stirred for 24 hours at 23° C. and for 48 hrs at 37° C. The reaction mixture was then diluted with 1X 0.9% saline, the unreacted aldehyde groups were "capped" with 1 molar equivalent sodium borohydride $NaBH_4$. The capping reaction time was 3 hours.

Example 4: Conjugate Purification

The capped reaction mixture was filtered using a 5 μm filter and then purified using 100K MWCO ultra filtration membranes. The conjugate was first diafiltered using 10 mM succinate/0.9% saline, pH 6.0 buffer. The purified conjugate was then filtered through 0.45/0.22 μm filters to obtain the bulk conjugate.

Example 5: Degree of Oxidation

Figure 2:
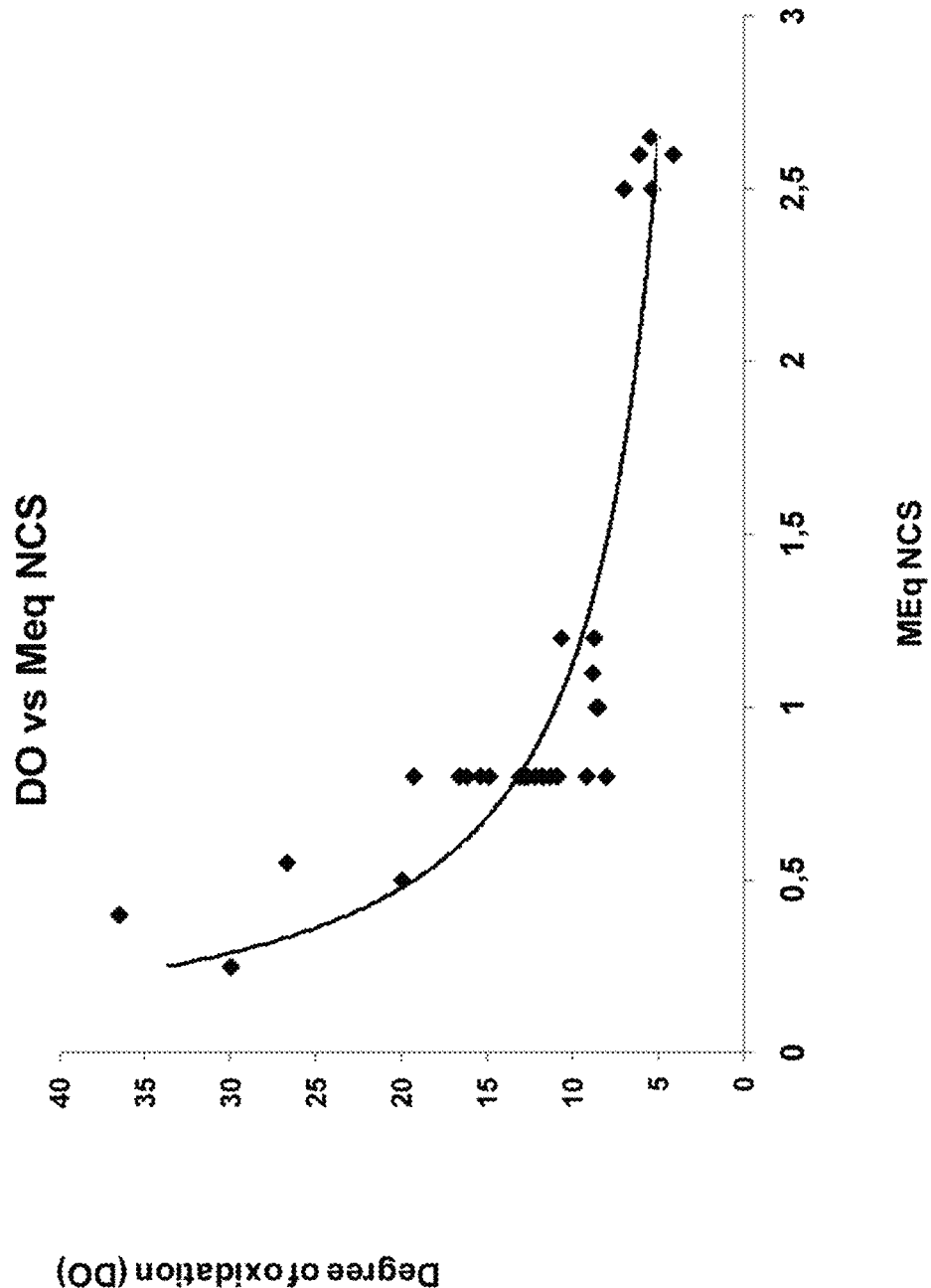
FIG. 2 shows the dependence of N-Chlorosuccinimide in the Tempo/NCS oxidation reaction on the degree of oxidation (DO).

Successful oxidation of primary alcohols in the Serotype 12F polysaccharide was achieved using the TEMPO/NCS system. The hydrolyzed Serotype 12F polysaccharides were oxidized to varying degrees of oxidation (DO) levels by adjusting the amount of NCS cooxidant. The effect on DO by varying amounts of NCS using different polysaccharide batches and molecular weights is shown in FIG. 2. Typically 0.5-2.5 Molar Equivalents of NCS was used to achieve the target Degree of Oxidation. Typically the oxidation reaction is complete in 2 hours as no significant change in DO was observed after 2 hours.

Several Serotype 12F conjugates were generated and characterized using the TEMPO/NCS oxidized polysaccharide. The results are summarized in Table 1. Some representative conjugates were also successfully generated using other Pneumococcal serotypes activated with TEMPO/NCS system. The procedure for the generation of conjugates for other Pneumococcal serotypes was the same as the method used for Serotype 12F. The results are described in Tables 2 to 4.

TABLE 1

Pneumococcal Serotype 12F-CRM$_{197}$ conjugates

| | Conjugate Batch | | | | | |
|---|---|---|---|---|---|---|
| | 12F-84A | 12F-97B | 12F-147C | 12F-171D | 12F-177-6E | 12F-181F |
| Oxidation Time (hr) | 2 | 2 | 4 | 2 | 2 | 2 |
| Degree of Oxidation (D.O) | 12.0 | 6.0 | 9.6 | 12.0 | 11.5 | 11.5 |
| % Activated Saccharide Yield | 80 | 71 | 70 | 89 | 86 | 86 |
| Activated Saccharide MW by MALLS (kDa) | 137 | 155 | 170 | 190 | 240 | 240 |
| Conjugation process | Lyo-CRM | Lyo-CRM | Lyo-CRM | Lyo-CRM | Lyo-CRM | Co-Lyo |
| Conjugate Results | | | | | | |
| Saccharide yield (%) | 51.6 | 76.8 | 53.6 | 76.3 | 65.8 | 40.7 |
| Saccharide/Protein Ratio | 1.2 | 0.9 | 1.0 | 1.1 | 1.4 | 0.9 |
| % Free Saccharide | 24 | 10 | 17 | 20 | 23 | 14 |
| Mw by SEC-MALLS (kDa) | 2050 | 3000 | 3600 | 1500 | 2400 | 2100 |

TABLE 2

Pneumococcal Serotype 3-CRM$_{197}$ conjugates

| Conjugate Batch | Pn3-106-1 | Pn3-106-4 |
|---|---|---|
| Polysaccharide MALLS (Mw) kDa | 430 | 430 |
| Oxidation | | |
| Oxidation Time (hr) | 2 | 2 |
| D.O. | 9.4 | 15 |
| % Activated Saccharide Yield | 55 | 65 |
| Activated Saccharide MW by SEC-MALLS (kDa) | 340 | 360 |
| Conjugation | | |
| Conjugate Results | | |
| Saccharide yield (%) | 29.9 | 55.0 |
| Saccharide-Protein Ratio | 0.7 | 1.6 |
| % Free Saccharide | 21.0 | 30.0 |
| MW by SEC-MALLS (kDa) | 2100 | 2600 |

TABLE 3

Pneumococcal Serotype 33F-CRM$_{197}$ Conjugates

| Conjugate Batch | 33F-#55 | 33F-#63 |
|---|---|---|
| Polysaccharide MALLS (Mw) | 128 kDa | 150 kDa |
| D.O. | 20 | 5 |
| Yield | 92% | 97% |
| Saccharide yield (%) | 44% | 68% |
| Saccharide-Protein Ratio | 0.54 | 0.68 |
| Free Saccharide | <1% | 1.10% |
| Free Protein | <1% | <1% |
| Mw by SEC-MALLS (kDa) | 11160 kDa | 2730 kDa |

TABLE 4

Pneumococcal Serotype 10A Conjugates

| Conjugate Batch | 10A-#77 | 10A-#78 | 10A-#85 | 10A-#88 | 10A-#89 | 10A-#103 | 10A-#104 |
|---|---|---|---|---|---|---|---|
| Polysaccharide MALLS (Mw) | 538 Kda | 538 Kda | 538 Kda | 538 Kda | 538 Kda | 509 Kda | 509 Kda |
| D.O. | 7.9 | 24 | 12 | 6.9 | 10 | 11.3 | 5.7 |
| Yield | 82% | 90% | 94% | 88% | 94% | 94% | 86% |
| Saccharide yield (%) | 35 | 20 | 42 | 35 | 41 | 43 | 36 |
| Saccharide-Protein Ratio | 0.53 | 0.33 | 0.73 | 0.7 | 0.95 | 0.6 | 0.45 |
| Free Saccharide | <1 | 20 | 4.6 | 1.6 | 5.7 | <1 | <1 |
| Free Protein | <1% | <1% | <1% | <1% | <1% | <1% | <1% |
| Mw by SEC-MALLS | 3168 | 16390 | 4117 | 3137 | 2855 | 4380 | 3772 |

Example 6: Immunogenicity of Pn-serotype 12F-CRM$_{197}$ Conjugates using the TEMPO/NCS Oxidation Method The opsonophagocytic activity (OPA) titers for Serotype 12F-CRM$_{197}$ conjugates in mice were determined in mice under standard conditions. OPA titers (geometric mean titer (GMT) with 95% confidence interval (CI)) at four and seven weeks are shown in Table 5, demonstrating that the serotype 12F-CRM$_{197}$ conjugate (Batch 12F-97B; also see Table 1 for characterization data of this conjugate) elicited OPA titers in a murine immunogenicity model. The conjugate generated by the TEMPO-NCS was more immunogenic than the control conjugate (171B) generated from the periodate oxidation.

TABLE 5

Immunogenicity of Serotype 12F-CRM197 Conjugates

| Conjugate Sample/Dose | 0.001 ug | 0.01 ug | 0.1 ug |
|---|---|---|---|
| Periodate Oxidation (171B) Control | 4 | 16 | 172 |
| TEMPO/NCS Oxidation (12F-97B) | 40 | 417 | 880 |

Figure 6:
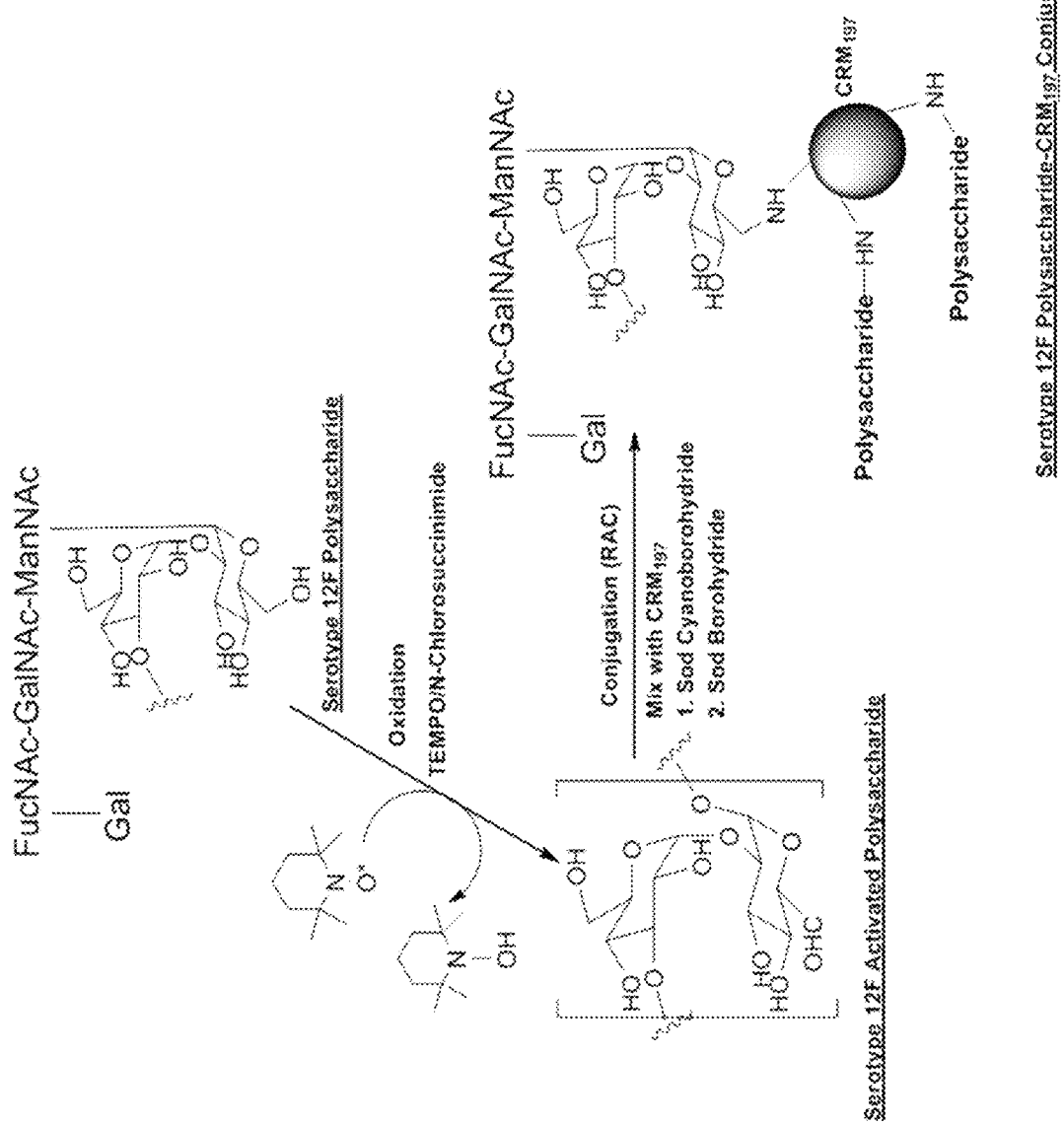
FIG. 6 shows the putative mechanism of oxidation/conjugation of Pn-serotype 12F using TEMPO/NCS.

Example 7: Putative Mechanism for the Pn-serotype 12F Conjugate Using Nitroxyl Radical in the Presence of an Oxidant Such as TEMPO/NCS The putative mechanism of oxidation/conjugation of Pn-serotype 12F is shown in FIG. 6. The primary hydroxyl groups of the polysaccharide are oxidized by catalytic amounts of nitroxyl radical such as TEMPO, with an oxidant such as NCS as the stoichiometric oxidant. The actual oxidant is the N-oxoammonium salt, in a catalytic cycle. The oxidation of the C-6 primary hydroxyl groups generates aldehyde groups which are subsequently reacted with the primary amino groups of the lysine of the carrier protein (CRM$_{197}$) to generate the glycoconjugate.

Example 8: Stability Comparison

Figure 7:
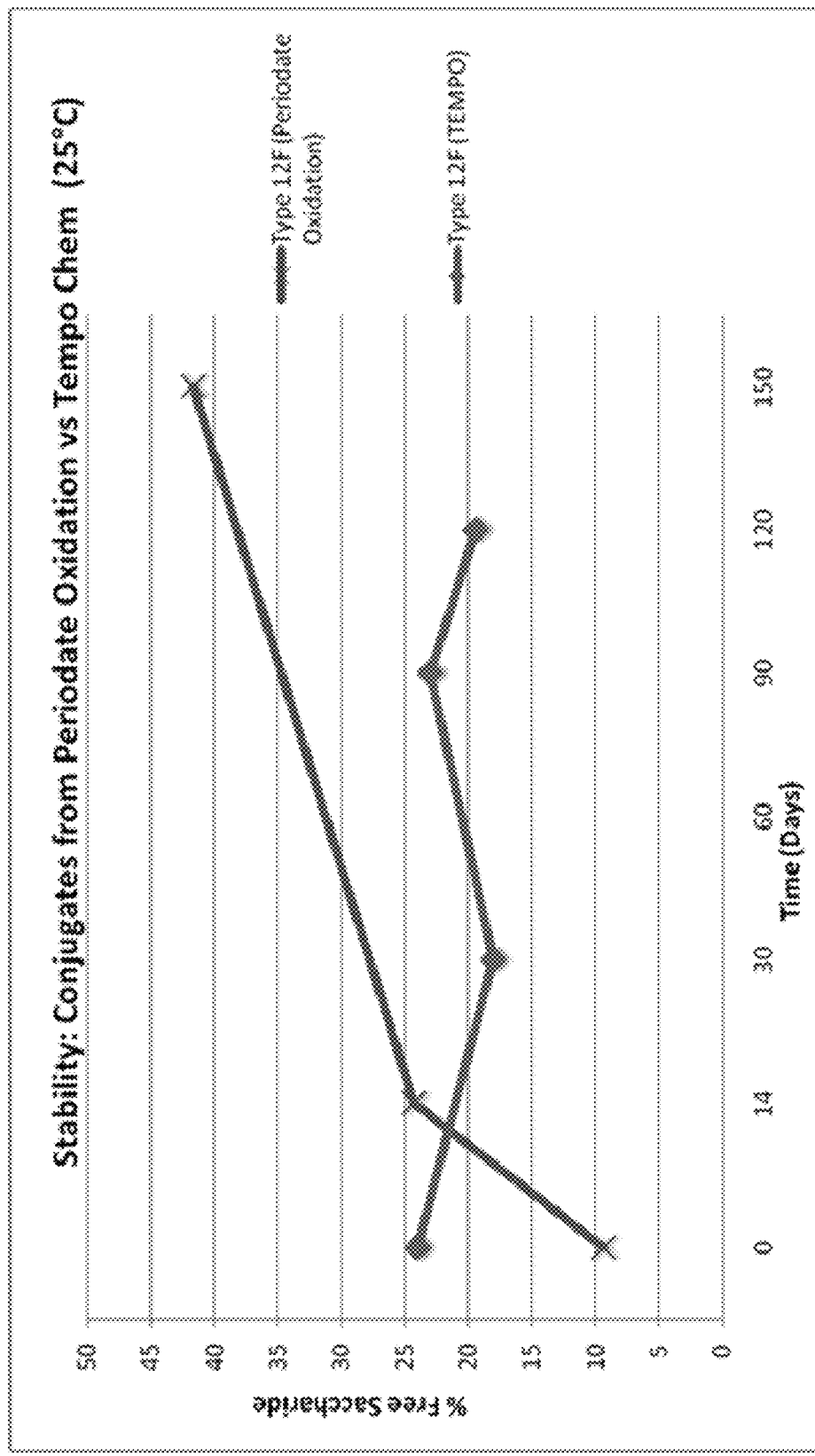
FIG. 7 shows the stability comparison of Pn-serotype 12F conjugates prepared using periodate oxidation vs. TEMPO/NCS oxidation.

Comparison of the stability (at 25° C.) of the conjugates generated by periodate oxidation vs TEMPO/NCS oxidation (see FIG. 7) demonstrated that the conjugate generated by the oxidation of the Pn-12F polysaccharides were relatively more stable. As shown in FIG. 7, an increase in the free saccharide over time was observed for the glycoconjugate generated by the periodate oxidation of the Pn-12F polysaccharide at 25° C. In contrast, the glycoconjugate prepared using the TEMPO/NCS oxidation of the Pn-12F polysaccharide showed no significant trends for the free saccharide under similar conditions.

The invention claimed is:

1. An immunogenic composition comprising a glycoconjugate comprising a *S. pneumoniae* serotype 12F capsular polysaccharide conjugated via an oxidized primary hydroxyl group to a carrier protein, wherein the oxidized primary hydroxyl group is present on an α-D-Glop or a 2-Glcp sugar residue of said *S. pneumoniae* serotype 12F capsular polysaccharide, wherein said glycoconjugate has a molecular weight of between about 500 kDa and about 5,000 kDa and a saccharide:carrier protein ratio (w/w) between 0.2 and 4, wherein the amount of free *S. pneumoniae* serotype 12F polysaccharide in the composition is less than about 35% free saccharide relative to total *S. pneumoniae* serotype 12F polysaccharide.

2. The immunogenic composition of claim 1, wherein said *S. pneumoniae* serotype 12F capsular polysaccharide has a molecular weight of between about 50 kDa and about 500 kDa.

3. The immunogenic composition of claim 1, wherein said *S. pneumoniae* serotype 12F capsular polysaccharide has a molecular weight of between about 90 kDa and about 250 kDa.

4. The immunogenic composition of claim 1, wherein said saccharide:carrier protein ratio (w/w) is between 0.9 and 1.7.

5. The immunogenic composition of claim 1, wherein said saccharide:carrier protein ratio (w/w) is between 1.1 and 1.7.

6. The immunogenic composition of claim 1, wherein said glycoconjugate has a molecular weight of between about 1000 kDa and about 3600 kDa.

7. The immunogenic composition of claim 1, wherein said glycoconjugate has a molecular weight of between about 1000 kDa and about 3000 kDa.

8. The immunogenic composition of claim 1, wherein the amount of free *S. pneumoniae* serotype 12F polysaccharide in the composition is less than 35% when maintained at 25° C. for 120 days from when it was prepared.

9. The immunogenic composition of claim 1, wherein the amount of free *S. pneumoniae* serotype 12F polysaccharide in the composition is less than 30% when maintained at 25° C. for 120 days from when it was prepared.

10. The immunogenic composition of claim 1, wherein the amount of free *S. pneumoniae* serotype 12F polysaccharide in the composition is less than 25% when maintained at 25° C. for 120 days from when it was prepared.

11. The immunogenic composition of claim 1, wherein said carrier protein is a toxoid.

12. The immunogenic composition of claim 1, wherein said carrier protein is a toxin from tetanus, diphtheria, pertussis, *Pseudomonas*, *E. coli*, *Staphylococcus* or *Streptococcus*.

13. The immunogenic composition of claim 1, wherein said carrier protein is CRM$_{197}$.

14. The immunogenic composition of claim 1, further comprising a pharmaceutically acceptable excipient, carrier, or diluent.

15. The immunogenic composition of claim 1, further comprising an additional antigen.

16. The immunogenic composition of claim 15, wherein the additional antigen comprises a protein antigen or a glycoconjugate of a capsular polysaccharide derived from *S. pneumoniae*.

17. The immunogenic composition of claim 16, wherein the additional antigen comprises a glycoconjugate of a capsular polysaccharide selected from *S. pneumoniae* serotypes 1, 4, 5, 6A, 6B, 7F, 8, 9V, 11A, 14, 15B, 18C, 19A, 19F, 22F, and 23F capsular polysaccharides.

18. The immunogenic composition of claim 1, further comprising a glycoconjugate of a capsular polysaccharide from a *S. pneumoniae* serotype selected from the group of serotypes consisting of 1, 3, 4, 5, 6A, 6B, 7F, 8, 9V, 10A, 11A, 14, 15B, 18C, 19A, 19F, 22F, 23F, and 33F.

19. The immunogenic composition of claim 1, further comprising an adjuvant.

20. The immunogenic composition of claim 19, wherein the adjuvant is an aluminum-based adjuvant selected from aluminum phosphate, aluminum sulfate, and aluminum hydroxide.

21. The immunogenic composition of claim 18, further comprising glycoconjugates of capsular polysaccharide from *S. pneumoniae* serotypes 1, 3, 4, 5, 6A, 6B, 7F, 8, 9V, 10A, 11A, 14, 15B, 18C, 19A, 19F, 22F, 23F, and 33F.

22. An immunogenic composition comprising a glycoconjugate comprising a *S. pneumoniae* serotype 12F capsular polysaccharide conjugated via an oxidized primary hydroxyl group on an α-D-Glcp or a 2-Glcp sugar residue to a carrier protein.

23. The immunogenic composition of claim 22, wherein said carrier protein is $CRM_{197}$.

24. The immunogenic composition of claim 23, wherein the amount of free *S. pneumoniae* serotype 12F polysaccharide in the composition is less than about 35% free saccharide relative to total *S. pneumoniae* serotype 12F polysaccharide.

25. The immunogenic composition of claim 24, wherein the amount of free *S. pneumoniae* serotype 12F polysaccharide in the composition is less than 35% when maintained at 25° C. for 120 days from when it was prepared.

\* \* \* \* \*